United States Patent
Patoiseau et al.

(10) Patent No.: US 6,583,159 B1
(45) Date of Patent: Jun. 24, 2003

(54) SUBSTITUTE 1-(PIPERIDIN-4-YL)-3-(ARYL)-ISOTHIOUREAS, THEIR PREPARATION AND THERAPEUTIC USE

(75) Inventors: Jean-François Patoiseau, Castres (FR); Jean-Pierre Rieu, Castres (FR); Gareth John, Castres (FR); Bruno Legrand, Lautrec (FR); Yvan Verscheure, Castres (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 0 days.

(21) Appl. No.: 09/889,811
(22) PCT Filed: Jan. 21, 2000
(86) PCT No.: PCT/FR00/00136
  § 371 (c)(1),
  (2), (4) Date: Jul. 20, 2001
(87) PCT Pub. No.: WO00/43011
  PCT Pub. Date: Jul. 27, 2000

(30) Foreign Application Priority Data

Jan. 22, 1999 (FR) .............................. 99 00705

(51) Int. Cl.$^7$ ..................... A61K 31/445; C07D 211/68
(52) U.S. Cl. ...................................... 514/317; 546/194
(58) Field of Search ............... 514/329, 317; 546/223, 194

(56) References Cited

FOREIGN PATENT DOCUMENTS

WO 9705134 * 2/1997

* cited by examiner

Primary Examiner—Alan L. Rotman
Assistant Examiner—Binta Robinson
(74) Attorney, Agent, or Firm—The Firm of Hueschen and Sage

(57) ABSTRACT

The invention concerns compounds of formula (I) wherein: R1 and R2, identical or different, represent a saturated or unsaturated alkyl radical, branched or not and containing 1 to 7 carbon atoms; R3 to R8, identical or different, represent a hydrogen, an alkyl branched or not and containing 1 to 5 carbon atoms, an acyloxy, branched or not and containing 1 to 5 carbon atoms, a halogeno, nitro, hydroxy, acyl or alkoxy group containing 1 to 5 carbon atoms, a dialkylamino group containing 1 to 5 carbon atoms, a trifluoromethyl or trifluoro methoxyl group; Z represents an oxygen or sulphur atom or methylene; m represents an integer between 0 and 4 inclusively; n represents an integer between 2 and 7 inclusively; and their pure enantiomers and mixtures, the therapeutically acceptable mineral or organic salts of the compounds of formula (I) and their possible hydrates.

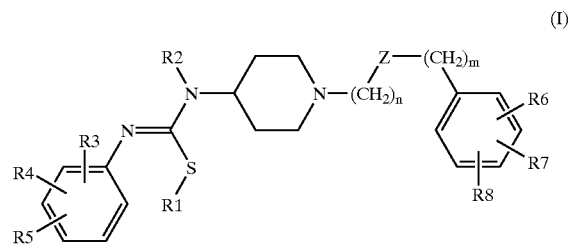

7 Claims, No Drawings

SUBSTITUTE 1-(PIPERIDIN-4-YL)-3-(ARYL)-ISOTHIOUREAS, THEIR PREPARATION AND THERAPEUTIC USE

The invention relates to novel substituted 1,2-dialkyl-1-[1-[aryl(alkyl)oxyalkyl]piperidin-4-yl]-3-arylisothioureas, to their process of preparation and to their use as medicament.

A previous patent of the Applicant Company (WO-97/05134) claimed N-alkyl-N-[1-((ω-aryloxyalkyl)piperidin-4-yl]-4H-3,1-benzothiazin-2-amine derivatives having therapeutic interest, particularly in the treatment of myocardial ischemia.

In order to bring about greater flexibility in the active molecule, capable of increasing its bioavailability and its solubility, the "open" compounds of the preceding series of benzothiazines were synthesized and allowed a novel class of compounds to be identified which is a subject-matter of the present invention: substituted 3-aryl-1-(piperidin-4-yl)-1-alkylisothioureas. Their pharmacological study has generally shown an activity greater than that of the cyclic series based on the in vitro test of contraction with veratrine of the rat isolated left atrium and in the ischemia test on the perfused isolated heart of the guinea pig.

Claimed Molecules

The molecules of the present invention belong to the class of the N- and S-substituted 1-(1-aryl(alkyl)oxyalkylpiperidin-4-yl)-3-arylisothioureas of formula I:

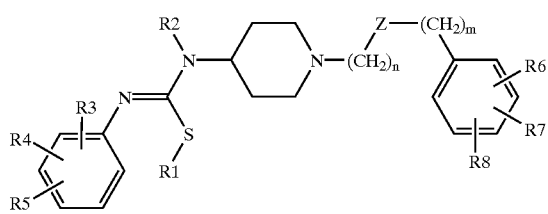

(I)

in which:

$R_1$ and $R_2$, which are identical or different, represent a saturated or unsaturated and branched or unbranched alkyl radical having from 1 to 7 carbon atoms, $R_3$ to $R_8$, which are identical or different, represent:
a hydrogen,
a branched or unbranched alkyl having from 1 to 5 carbon atoms,
a branched or unbranched alkyloxy having from 1 to 5 carbon atoms,
a halo group,
a nitro group,
a hydroxyl group,
an acyl or acyloxy group having from 2 to 5 carbon atoms,
a dialkylamino group having from 1 to 5 carbon atoms,
a trifluoromethyl or trifluoromethoxyl group,
Z represents an oxygen or sulfur atom or a methylene,
m represents an integer varying from 0 to 4 inclusive,
n represents an integer between 2 and 7 inclusive.

The invention relates just as well, when they exist, to the pure R or S isomers or their mixtures.

The present invention includes the therapeutically acceptable inorganic or organic salts of the compounds of formula I and their possible hydrates.

The invention also relates to the process for the preparation of the claimed compounds and to their application as medicaments.

The molecules of the present invention possess noteworthy cytoprotective properties superior to those of the cyclic series of the family of the 4H-3,1-benzothiazin-2-amines and of the reference products, such as R56865.

Synthesis of the Compounds of Formula I

The 1,2-dialkyl-1-[1-[aryl(alkyl)oxyalkyl]piperidin-4-yl]-3-arylisothioureas (I) are prepared in two stages from the N-alkyl-N-[1-(aryl)oxyalkyl-piperidin-4-yl]amines (II). The condensation of these amines (II) with an aryl isothiocyanate (III) according to the method of Kaye and Parris (*J. Org. Chem.*, 1951, 16, 1859–1863) provides the corresponding thiourea (IV).

The S-alkylation of the latter is carried out by condensation of a haloalkane or of a dialkyl sulfate, either by adapting the method of Dupin S. and Pesson M. (*Bull. Soc. Chim. Fr.*, 1963, 144–150) or by using calcium oxide to block the iodides formed by extrapolating the method of Honkenen. E. et al. (*J. Med. Chem.*, 1983, 26, 1433–38), to give directly the compound I of the present invention (cf. Scheme 1).

Scheme 1

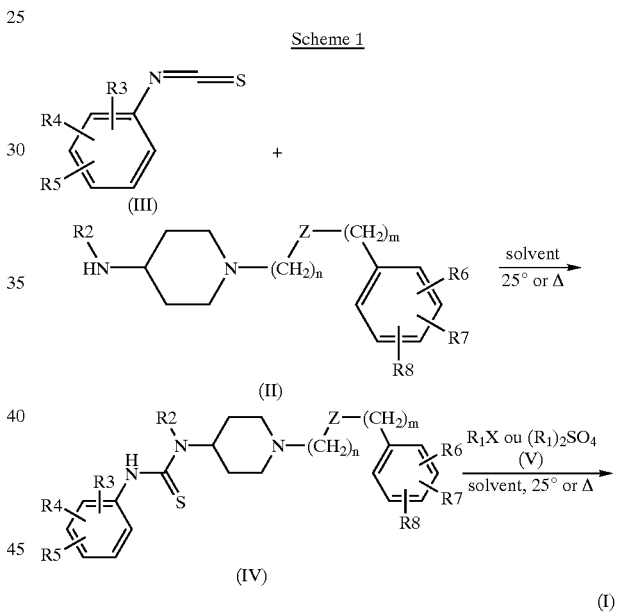

In the case where m=0 (Scheme 2), the intermediate amines (II) were prepared according to Ismaiel A. M. (*J. Med. Chem.*, 1993, 36, 2519–2525) as described above in Patent WO 97/05134, using sodium triacetoxyborohydride as reducing agent in the final stage according to Abdel-Magid A. F. et al. (*J. Org. Chem.*, 1996, 61, 3849–3862).

Scheme 2

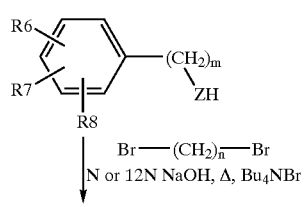

-continued

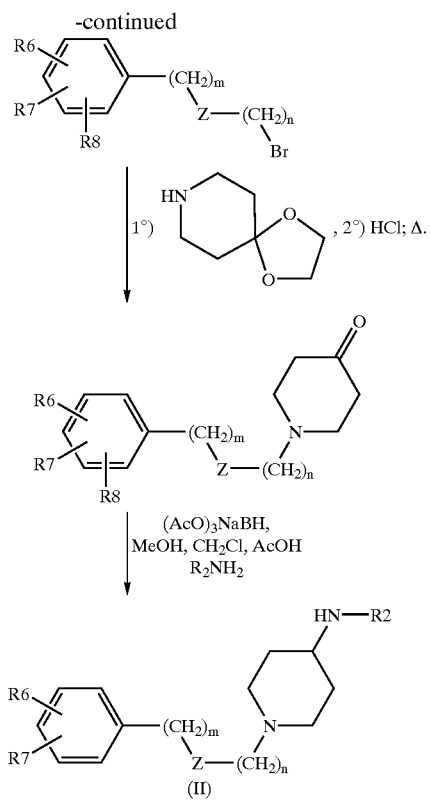

If m≠0, the etherification reaction (first stage, Scheme 2) can be carried out starting from the corresponding alcohol with 50% sodium hydroxide solution by PTC according to Burgstahler et al., *J. Org. Chem.*, 1977, 42, 566–8.

The phenyl isothiocyanates which are not available commercially are prepared from the corresponding anilines by using thiocarbonyldiimidazole as described by Staab H. A. and Walther G. (*Liebigs Ann. Chem.*, 1962, 567, 104-[lacuna]).

EXAMPLE 1

1,2-Dimethyl-3-phenyl-1-[1-[4-(3,4-difluorophenoxy)butyl]piperidin-4-yl]isothiourea hydrogen fumarate (1)

1.1)
1-Methyl-3-phenyl-1-[1-[4-(3,4-difluorophenoxy)butyl]piperidin-4-yl]thiourea (1.1)

A mixture formed of 2 g (14.8 mmol) of phenyl isothiocyanate, 5.5 g (14.8 mmol) of N-methyl-1-[4-(3,4-difluorophenoxy)butyl]piperidin-4-ylamine dihydrochloride (cf. WO 97/05134) and 4.1 ml (29.6 mmol) of triethylamine in 25 ml ethanol is brought to reflux for 2 h. After returning to 25° C., the mixture is evaporated to dryness and the residue is taken up in 30 ml of water and extracted with methylene chloride. The organic phase is washed with water and with aqueous saline solution and then dried over anhydrous sodium sulfate. After removing the insoluble inorganic material, the filtrate is evaporated to dryness to give a cream solid (m=5.9 g) which, triturated in isopropyl alcohol, gives 5.3 g (Yd: 83%) of off-white powder of formula 1.1.

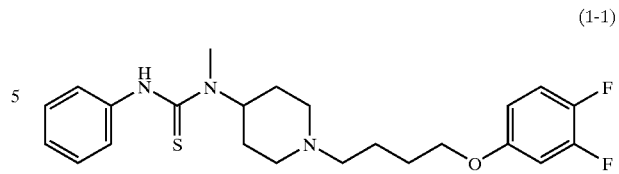

(1-1)

Empirical formula: $C_{23}H_{29}F_2N_3OS$
Molecular mass: 433.54
Melting point: 152–3° C.
NMR (d$_6$-DMSO) δ: 1.4–1.85 (m, 8H), 1.93 (m, 2H), 2.33 (m, 2H), 2.95 (m, 2H), 3.03 (s, 3H), 3.98 (t, 2H), 5.04 (m, 1H), 6.7–6.9 (m, 1H), 7.02–7.2 (m, 2H), 7.25–7.4 (m, 5H), 9 (s, 1H).

1.2) 1,2-Dimethyl-3-phenyl-1-[1-[4-(3,4-difluorophenoxy)butyl]piperidin-4-yl]isothiourea hydrogen fumarate (1)

A solution of 2 g (4.6 mmol) of the preceding urea (1.1) in a mixture of 30 ml of dichloromethane and 40 ml of ethanol is treated in a 100 ml round-bottomed flask with 302 μl (0.69 g or 4.84 mmol) of methyl iodide and stirred overnight at 25° C. The mixture is evaporated to dryness is taken up in dichloromethane and water. The organic phase is separated, washed with aqueous saline solution and dried over anhydrous sodium sulfate. The insoluble inorganic material is filtered off and the filtrate is evaporated to dryness: yellow oil (2 g). This oil is purified by flash chromatography, elution being carried out with a 97.5/2.25/0.25 $CH_2Cl_2/CH_3OH/NH_4OH$ mixture. The fractions having the expected thiourea are evaporated: light yellow oil (m=2.1 g; Yd: 66%).

Hydrogen fumarate: 1.07 g of base in 20 ml of EtOH is stirred at 25° C.; the slight insoluble material is removed by filtration and then 278 mg of fumaric acid in 5 ml of hot alcohol are added to the preceding filtrate. After slow crystallization, the organic salt of formula 1 is collected by filtration and dried (m=825 mg; Yd: 40%):

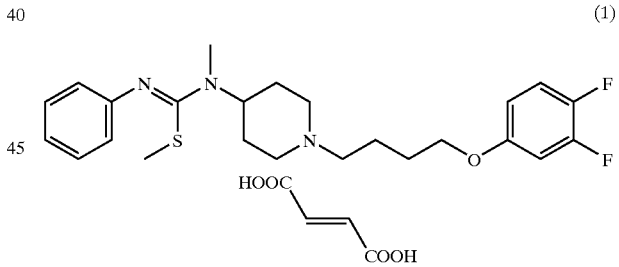

(1)

Empirical formula: $C_{28}H_{35}F_2N_3O_5S$
Molecular mass: 563.65
White crystals
Melting point: 151–152° C.
NMR (d$_6$-DMSO) δ: 1.5–1.8 (m, 6H), 1.85–1.95 (m, 2H), 2 (s, 3H), 2.25 (t, 2H), 2.45–2.65 (m, 2H), 2.9 (s, 3H), 3.05–3.15 (m, 2H), 3.97 (t, 2H), 4.1–4.3 (m, 1H), 6.57 (s, 2H), 6.76 (m, 3H), 6.9 (t, 1H), 7.0–7.12 (m, 1H), 7.2 (t, 2H), 7.44 (q, 1H), 12–13 (m, 2H).

EXAMPLE 2

2-Ethyl-1-[1-[4-(3,4-difluorophenoxy)butyl]piperidin-4-yl]-1-methyl-3-phenylisothiourea hydrogen fumarate (2)

A solution of 2 g (4.61 mmol) of 1-methyl-3-phenyl-1-[1-[4-(3,4-difluorophenoxy)butyl]piperidin-4-yl]thiourea (prepared in Example 1.1) in 30 ml of ethanol is treated with 387 μl (754 mg or 4.84 mmol) of iodoethane and stirred overnight at 25° C., then an additional 199 μl of iodoethane are again added and the mixture is stirred for a further 24 h. The mixture is evaporated to dryness; an insoluble material, formed by the hydroiodide of the starting thiourea, is removed by tritutration in ether. The ethereal filtrate is evaporated to dryness and the residue is taken up in methylene chloride and a 2N sodium hydroxide solution. The phases are separated and the aqueous phase is reextracted with CH$_2$Cl$_2$. The combined organic phase is washed with water and with aqueous saline solution, dried over anhydrous sodium sulfate and evaporated to dryness and the residue is purified by flash chromatography in the usual way to give a pale yellow oil (m=1.3 g, Yd: 61%); the base is subsequently salified with fumaric acid as described in Example 1.2 to give 1.31 g (Yd 48%) of crystals of formula 2.

(2)

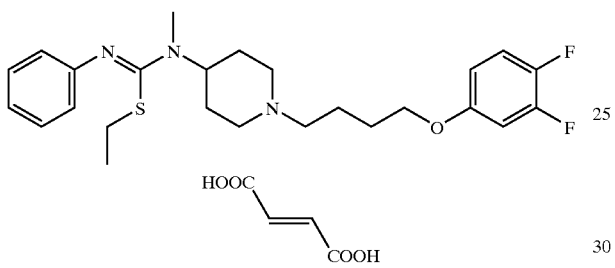

Empirical formula: C$_{29}$H$_{37}$F$_2$N$_3$O$_5$S
Molecular mass: 577.57
White crystals
Melting point: 151–152° C.
NMR (d$_6$-DMSO) δ: 1.05 (t, 3H), 1.5–1.8 (m, 6H), 1.80–2.05 (m, 2H), 2.23 (t, 2H), 2.38 (q, 2H), 2.45–2.6 (m, 2H), 2.9 (s, 3H), 3.05–3.15 (m, 2H), 3.97 (t, 2H), 4.2–4.4 (m, 1H), 6.75 (s, 2H), 6.76 (d, 2H), 6.90 (t, 1H), 7–7.1 (m, 1H), 7.2 (t, 2H), 7.33 (q, 1H).

EXAMPLE 3

1-Ethyl-1-[1-[4-(3,4-difluorophenoxy)butyl] piperidin-4-yl]-2-methyl-3-phenylisothiourea hydrogen fumarate (3)

3.1) 4-Ethylamino-1-[4-(3,4-difluorophenoxy)butyl] piperidine hydrochloride (3.1)

A solution of 6 g of 1-[4-(3,4-difluorophenoxy)butyl] piperidin-4-one (21.2 mmol), prepared as described in Patent WO 97/05134, in a mixture of 70 ml of CH$_2$Cl$_2$ and 5 ml of MeOH is treated with 1.73 g (21.2 mmol) of ethylamine hydrochloride. The mixture is stirred for 2 h at 25° C. and then cooled on an ice bath, and then 5.39 g (25.4 mmol) of sodium triacetoxyborohydride and 1.25 ml of acetic acid are added dropwise. After stirring for 1 h at 0° C., the mixture is allowed to return to 25° C. and is stirred overnight at this temperature. The reaction mixture is poured into ice and basified (with 2N sodium hydroxide) to pH=12. Extraction is carried out several times with methylene chloride and then the extract is washed with water and with aqueous saline solution. After drying over anhydrous sodium sulfate, the inorganic salt is removed and the filtrate is evaporated to dryness to give 6.5 g of brown oil. This oil is taken up in 40 ml of ethanol and salified with an ethanolic hydrochloric acid solution to give 5.8 g (Yd: 71%) of compound of formula 3.1.

(3-1)

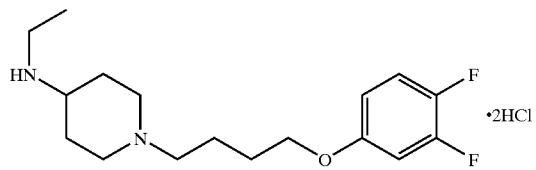

Empirical formula: C$_{17}$H$_{28}$Cl$_2$F$_2$N$_2$O
Molecular mass: 385.33
Off-white crystals
Melting point (dec.) 200° C.
NMR (d$_6$-DMSO) δ: 1.22 (t, 3H), 1.6–2.4 (m, 8H), 2.8–3.7 (m, 9H), 3.99 (t, 2H), 6.72–6.82 (m, 1H), 6.95–7.15 (m, 1H), 7.35 (q, 1H), 9.2–9.7 (m, 2H), 10.5–11.6 (m, 1H).

3.2) 1-Ethyl-1-[1-[4-(3,4-difluorophenoxy)butyl]piperidin-4-yl]-3-phenylthiourea (3.2)

By using the procedure described in Example 1.1 but starting from 1.4 g (10.4 mmol) of the preceding compound 3.1, the thiourea of formula 3.2 is prepared with a yield of 83%:

(3-2)

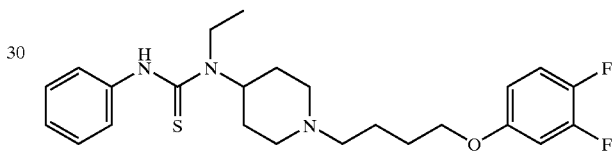

Empirical formula: C$_{24}$H$_{31}$F$_2$N$_3$OS
Molecular mass: 447.57
Light beige powder
Melting point: 133–134° C.
NMR (d$_6$-DMSO) δ: 1.15 (t, 3H), 1.4–1.8 (m, 8H), 1.85–2 (m, 2H), 2.31 (t, 2H), 3.6 (q, 2H), 3.98 (t, 2H), 5.03 (m, 1H), 6.7–6.8 (m, 1H), 7.02–7.18 (m, 2H), 7.2–7.4 (m, 5H), 8.89 (s, 1H).

3.3) 1-Ethyl-1-[1-[4-(3,4-difluorophenoxy)butyl]piperidin-4-yl]-2-methyl-3-phenylisothiourea hydrogen fumarate (3)

By carrying out the preparation as described in Example 1.2 starting from 2 g of the preceding thiourea 3.2, the compound of formula 3 is prepared with a yield of 48%:

(3)

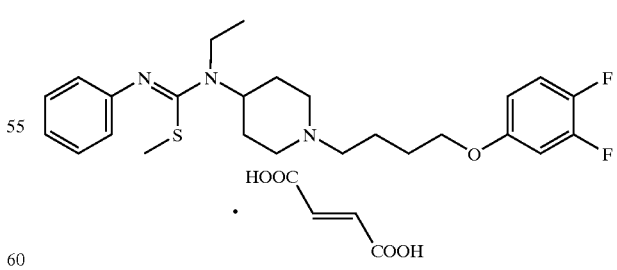

Empirical formula: C$_{29}$H$_{37}$F$_2$N$_3$O$_5$S
Molecular mass: 577.67
White crystals
Melting point: 120–121° C.
NMR (d$_6$-DMSO) δ: 1.12 (t, 3H), 1.5–1.95 (m, 6H), 1.90 (s, 3H), 2.23 (t, 2H), 2.45–2.6 (m, 2H), 3.10 (d, d, 2H), 3.25–3.6 (m, 2H), 3.97 (t, 2H), 4.1–4.3 (m, 1H), 6.57 (s, 2H), 6.7–6.85 (m, 2H), 6.89 (t, 1H), 7.02–7.1 (m, 1H), 7.23 (t, 2H), 7.28–7.4 (t d, 1H).

EXAMPLE 4

1-Isobutyl-1-[1-[4-(3,4-difluorophenoxy)butyl]-piperidin-4-yl]-2-methyl-3-phenylisothiourea hydrogen fumarate (4)

4.1) 4-Isobutylamino-1-[4-(3,4-difluorophenoxy)butyl] piperidine dihydrochloride (4.1)

The reductive amination, carried out as described in Example 3.1 but starting from 1.67 ml (1.3 g or 16.8 mmol) of isobutylamine, makes it possible to prepare 5.2 g (Yd 75%) of the dihydrochloride of formula 4.1:

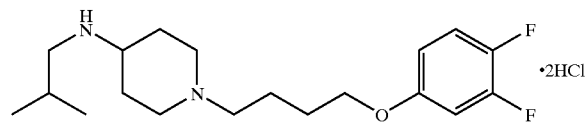
(4-1)

Empirical formula: $C_{19}H_{32}Cl_2F_2N_2O$

Molecular mass: 413.38

Off-white crystals

Melting point (dec.): >205° C.

NMR (d$_6$-DMSO) δ: 0.96 (d, 6H), 1.6–1.85 (m, 4H), 1.9–2.15 (m, 2H), 2.2–2.3 (m, 2H), 2.7–3.25 (m, 7H), 3.5–3.7 (m, 2H), 3.99 (t, 2H), 6.6–6.8 (m, 1H), 7.03–7.12 (m, 1H), 7.3–7.4 (m, 1H), 9–9.3 (m, 2H), 10.6–11 (m, 1H).

4.2) 1-Isobutyl-1-[1-[4-(3,4-difluorophenoxy)butyl] piperidin-4-yl]-3-phenylthiourea (4.2)

The condensation of 1 g (7.4 mmol) of phenyl isothiocyanate with 3.06 g (7.4 mmol) of the preceding compound 4.1 according to the protocol of Example 1.7 gives 3.88 g (Yd 91%) of the corresponding thiourea of formula 4.2:

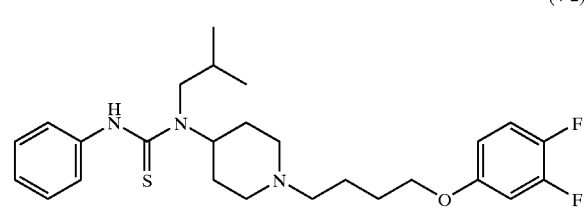
(4-2)

Empirical formula: $C_{26}H_{35}F_2N_3OS$

Molecular mass: 475.62

Off-white crystals

Melting point: 132° C.

NMR (d$_6$-DMSO) δ: 0.87 (d, 6H), 1.45–1.8 (m, 8H), 1.9 (t, 2H), 2–2.2 (m, 1H), 2.3 (t, 2H), 2.85–3 (m, 2H), 3.2–3.5 (m, 2H), 3.98 (t, 2H), 5 (m, 1H), 6.7–6.85 (m, 1H), 7–7.15 (m, 2H), 7.2–7.48 (m, 5H), 8.98 (s, 1H).

4.3) 1-Isobutyl-1-[1-[4-(3,4-difluorophenoxy)butyl] piperidin-4-yl]-2-methyl-3-phenylisothiourea hydrogen fumarate (4)

The S-methylation of 1.5 g (3.15 mmol) of the preceding thiourea 4.2 according to the protocol of Example 1.2 gives 620 mg (Yd: 34%) of the isothiourea of formula 4:

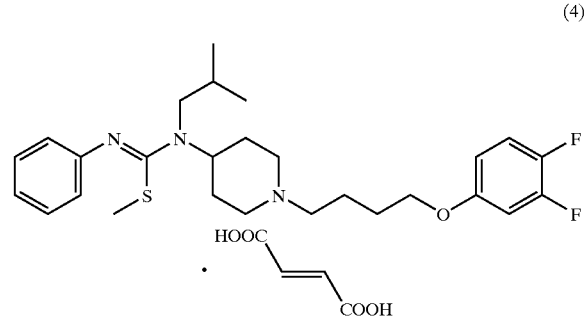
(4)

Empirical formula: $C_{31}H_{41}F_2N_3O_5S$

Molecular mass: 605.73

White crystals

Melting point: 131–132° C.

NMR (d$_6$-DMSO) δ: 0.84 (d, 6H), 1.5–2.05 (m, 9H), 2.01 (s, 3H), 2.134 (t, 2H), 2.45–2.6 (m, 2H), 3.05–3.15 (m, 4H), 3.97 (t, 2H), 4–4.1 (m, 1H), 6.58 (s, 2H), 6.7–6.8 (m, 3H), 6.91 (t, 1H), 7–7.09 (m, 1H), 7.22 (t, 2H), 7.28–7.4 (m, 1H), 11–13 (m, 2H).

EXAMPLE 5

1,2-Dimethyl-1-[1-[5-(3,4-difluorophenoxy)pentyl] piperidin-4-yl]-3-phenylisothiourea hydrogen fumarate (5)

5.1) 1-[5-(3,4-Difluorophenoxy)pentyl]piperidin-4-one (5.1)

The condensation of 14 g (50 mmol) of 4-(5-bromopentyloxy)-1,2-difluorobenzene with 7.13 g (50 mmol) of 1,4-dioxa-8-azaspiro[4.5]decane according to the process of Ismaiel A. M. et al. (J. Med. Chem., 1993, 36, 2519–25) gives, after deprotection, 13.6 g (Yd 91%) of an orangy oil of formula 5.1:

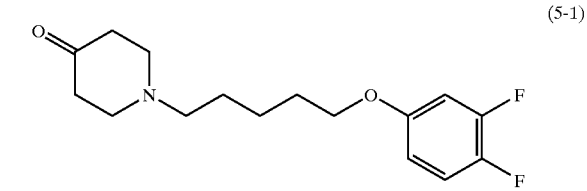
(5-1)

Empirical formula: $C_{16}H_{21}F_2NO_2$

Molecular mass: 297.34

NMR (CDCl$_3$) δ: 1.5–1.9 (m, 8H), 3–2.8 (m, 8H), 3.8–4 (m, 2H), 6.5–6.6 (m, 1H), 6.65–6.75 (m, 1H), 7–7.1 (m, 1H).

5.2) 1-[5-(3,4-Difluorophenoxy)pentyl]-4-methylamino] piperidine dihydrochloride 5.2

By starting from 10 g (33.6 mmol) of the preceding ketone 5.1 and 2.27 g (33.6 mmol) of methylamine hydrochlorde and by carrying out the reductive amination under the same conditions as those of Example 3.1, 7.8 g (Yd: 74%) of compound 5.2 are prepared:

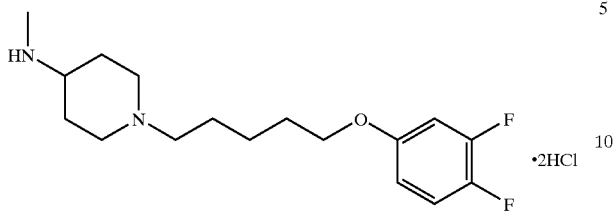

(5-2)

·2HCl

Empirical formula: $C_{17}H_{28}Cl_2F_2N_2O$
Molecular mass: 385.33
Cream crystals
Melting point (dec.): 202–205° C.
NMR ($d_6$-DMSO) δ: 1.3–1.45 (m, 2H), 1.65–1.8 (m, 4H), 1.9–2.05 (m, 2H), 2.2–2.6 (m, 2H), 2.51 (d, 3H), 2.85–3 (m, 5H), 3.5–3.6 (m, 2H), 3.97 (t, 2H), 6.7–6.8 (m, 1H), 7–7.12 (m, 1H), 7.34 (t.d, 1H), 9.2–9.7 (m, 2H), 10.6–11.2 (m, 1H).

5.3) 1-[1-[5-(3,4-Difluorophenoxy)pentyl]piperidin-4-yl]-1-methyl-3-phenylthiourea (5.3)

By applying the protocol of Example 1.1 to 1 g (7.4 mmol) of the preceding diamine 5.2, the compound of formula 5.3 is prepared with a yield of 91%:

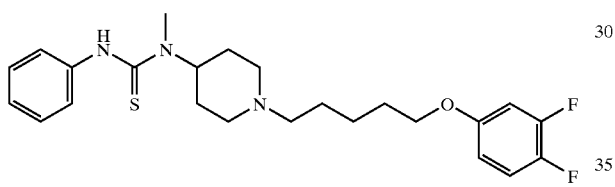

(5-3)

Empirical formula: $C_{24}H_{31}F_2N_3OS$
Molecular mass: 447.57
Cream crystals
Melting point: 90° C.
NMR (CDCl$_3$) δ: 1.4–1.6 (m, 4H), 1.7–1.9 (m, 6H), 2.1–2.2 (m, 2H), 2.3–2.5 (m, 2H), 2.9–3.1 (m, 5H), 3.9 (t, 2H), 5.2 (m, 1H), 6.5–6.6 (m, 1H), 6.64–6.75 (m, 1H), 7–7.1 (m, 2H), 7.15–7.3 (m, 3H), 7.3–7.6 (m, 2H).

5.4) 1,2-Dimethyl-1-[1-[5-(3,4-difluoro-phenoxy)pentyl]piperidin-4-yl]-3-phenylisothiourea hydrogen fumarate (5)

By reaction of 1.5 g of the preceding thiourea with 230 μl of methyl iodide according to the process of Example 1.2, 600 mg (Yd: 37%) of white crystals of formula 5 are prepared:

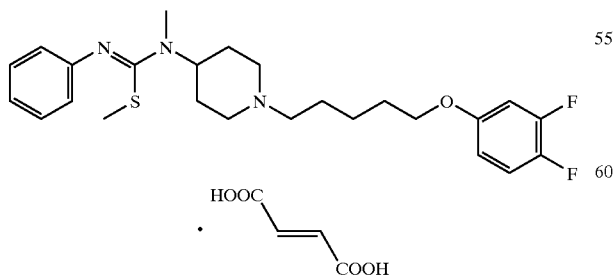

(5)

Empirical formula: $C_{29}H_{37}F_2N_3O_5S$
Molecular mass: 577.67

White powder
Melting point: 129–130° C.
NMR ($d_6$-DMSO) δ: 1.3–1.45 (m, 2H), 1.45–1.6 (m, 2H), 1.65–1.75 (m, 4H), 1.8–1.91 (m, 2H), 2 (s, 3H), 2.24 (t, 2H), 2.4–2.6 (m, 2H), 2.9 (s, 3H), 3.10 (d, 2H), 3.95 (t, 2H), 4.1–4.3 (m, 1H), 6.57 (s, 2H), 6.76 (d, 3H), 6.9 (t, 1H), 7.01–7.09 (m, 1H), 7.21 (t, 2H), 7.33 (q, 1H).

EXAMPLE 6

1,2-Dimethyl-1-[1-[3-(3,4-difluorophenoxy)propyl] piperidin-4-yl]-3-phenylisothiourea hydrogen fumarate (6)

6.1) 1-[1-[3-(3,4-Difluorophenoxy)propyl]piperidin-4-yl]-1-methyl-3-phenylthiourea (6.1)

The condensation of 2 g (14.8 mmol) of phenyl isothiocyanate with 5.3 g (14.8 mmol) of 1-[3-(3,4-difluorophenoxy)propyl]-4-(methylamino)piperidine dihydrochloride (cf. WO 97/05134) according to the process of Example 1.1 gives 5.5 g (Yd: 88%) of base thiourea crystals of formula 6.1:

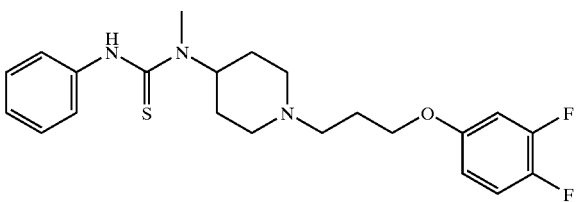

(6-1)

Empirical formula: $C_{22}H_{27}F_2N_3OS$
Molecular mass: 419.524
Off-white crystals
Melting point: 114–115° C.
NMR (CDCl$_3$) δ: 1.7–2.03 (m, 6H), 2.15 (t, 2H), 2.51 (t, 2H), 3–3.05 (m, 2H), 3.04 (s, 3H), 3.96 (t, 2H), 5.1–5.25 (m, 1H), 6.5–6.6 (m, 1H), 6.65–6.78 (m, 1H), 7–7.1 (m, 2H), 7.15–7.28 (m, 3H), 7.35 (t, 2H).

The hydrogen fumarate of the preceding base 6.1, prepared in the usual way in ethanol, melts at 159° C.

6.2) 1,2-Dimethyl-1-[1-[3-(3,4-difluorophenoxy)propyl] piperidin-4-yl]-3-phenylisothiourea hydrogen fumarate (6)

The S-methylation of 1.5 g (3.58 mmol) of the preceding thiourea 6.1 with 245 μl methyl iodide according to the protocol of example 1.2 gives 615 mg (Yd: 32%) of compound 6 of formula:

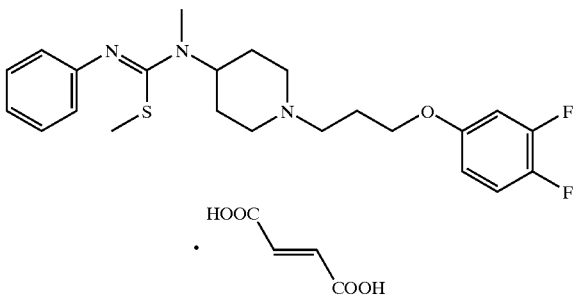

(6)

Empirical formula: $C_{27}H_{33}F_2N_3O_5S$
Molecular mass: 549.62
White crystals
Melting point: 106–107° C.

NMR (d$_6$-DMSO) δ: 1.66–1.7 (m, 2H), 1.75–1.95 (m, 4H), 2 (s, 3H), 2.05–2.2 (m, 2H), 2.45–2.6 (m, 2H), 2.9 (s, 3H), 3–3.1 (m, 2H), 4 (t, 2H), 4.07–4.25 (m, 1H), 6.59 (s, 2H), 6.76 (d, 3H), 6.9 (t, 1H), 7.02–7.1 (m, 1H), 7.20 (t, 2H), 7.33 (q, 1H), 12–14 (m, 2H).

EXAMPLE 7

1,2-Dimethyl-1-[1-[4-(4-fluorophenoxy)butyl] piperidin-4-yl]-3-phenylisothiourea hydrogen fumarate (7)

7.1) 1-Methyl-1-[1-[4-(4-fluorophenoxy)butyl]piperidin-4-yl]-3-phenylthiourea (7.1)

The condensation of 2 g (14.8 mmol) of phenyl isothiocyanate with 5.25 g (14.8 mmol) of 1-[4-(4-fluorophenoxy) butyl]-4-methylaminopiperidine dihydrochloride (cf. WO 97/05134) according to the protocol of Example 1.1 provides 5.5 g (Yd: 90%) of white crystals of formula 7.1:

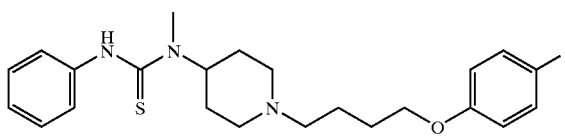

(7-1)

Empirical formula: C$_{23}$H$_{30}$FN$_3$OS
Molecular mass: 415.55
White crystals
Melting point: 161–162° C.
Hydrogen fumarate: M.p.=167° C.

NMR (d$_6$-DMSO) δ: 1.5–1.8 (m, 8H), 1.93 (t, 2H), 2.32 (t, 2H), 2.94 (d, 2H), 3.03 (s, 3H), 3.95 (t, 2H), 5.02 (m, 1H), 6.9–6.97 (m, 2H), 7.05–7.15 (m, 3H), 7.25–7.31 (m, 4H), 8.97 (s, 1H).

7.2) 1,2-Dimethyl-1-[1-4-(4-fluorophenoxy)butyl] piperidin-4-yl]-3-phenylisothiourea hydrogen fumarate (7)

The S-methylation of 1.5 g (3.6 mmol) of the preceding compound according to the procedure of Example 1.2 gives 620 mg (Yd: 32%) of white crystals of formula 7:

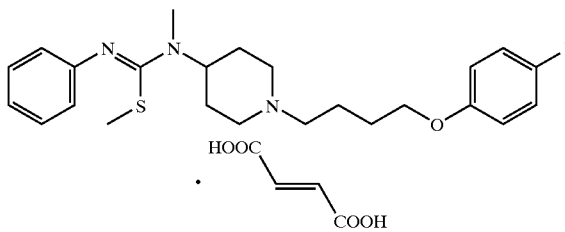

(7)

Empirical formula: C$_{28}$H$_{36}$FN$_3$O$_5$S
Molecular mass: 545.66
White crystals
Melting point: 133–134° C.

NMR (d$_6$-DMSO) δ: 1.5–1.73 (m, 6H), 1.8–1.93 (m, 2H), 2 (s, 3H), 2.24 (t, 2H), 2.4–2.6 (m, 2H), 2.89 (s, 3H), 3.05–3.5 (m, 1H), 3.95 (t, 2H), 4.1–4.3 (m, 1H), 6.58 (s, 2H), 6.76 (d, 2H), 6.8–7 (m, 3H), 7.05–7.15 (m, 2H), 7.20 (t, 2H).

EXAMPLE 8

1,2-Dimethyl-1-[1-[2-(4-fluorophenoxy)ethyl] piperidin-4-yl]-3-phenylisothiourea hydrogen fumarate (8)

8.1) 1-Methyl-1-[1-[2-(4-fluorophenoxy)ethyl]piperidin-4-yl-3-phenylthiourea (8.1)

The reaction of 680 mg (5 mmol) of phenyl isothiocynate with 1.63 g (5 mmol) of 1-[2-(4-fluorophenoxy)ethyl]-4-(methylamino)piperidine dihydrochloride according to the protocol of Example 1.2 gives 1.73 g (Yd: 89%) of beige powder of formula 8.1

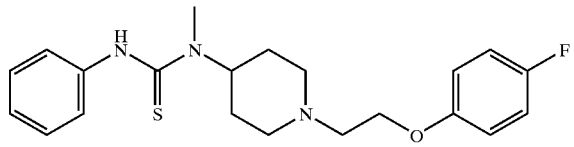

(8-1)

Empirical formula: C$_{21}$H$_{26}$FN$_3$OS
Molecular mass: 387.50
Beige powder
Melting point: 142° C.

NMR (CDCl$_3$) δ: 1.72–1.9 (m, 4H), 2.3 (t.d, 2H), 2.81 (t, 2H), 3.07 (s, 3H), 3.05–3.12 (m, 2H), 4.06 (t, 2H), 5.1–5.2 (m, 1H), 6.84 (d.d, 2H), 6.97 (t, 2H), 7.04 (s, 1H), 7.15–7.27 (m, 3H), 7.34 (t, 2H)

8.2) 1,2-Dimethyl-1-[1-[2-(4-fluorophenoxy)ethyl] piperidin-4-yl]-3-phenylisothiourea hydrogen fumarate (8)

By starting from 1.71 g (4.4 mmol) of the preceding thiourea 8.1 and by alkylating it with 290 μl of methyl iodide, 712 mg (Yd: 31%) of white crystals of formula 8 are prepared:

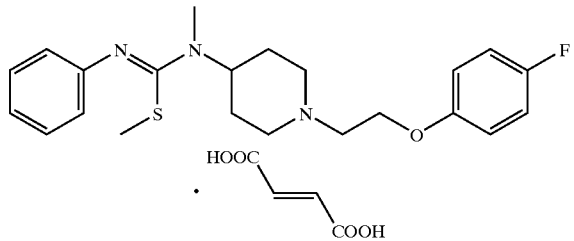

(8)

Empirical formula: C$_{26}$H$_{32}$FN$_3$O$_5$S
Molecular mass: 517.60
White crystals
Melting point: 120° C.

NMR (d$_6$-DMSO) δ: 1.5–1.7 (m, 2H), 1.75–1.9 (m, 2H), 1.99 (s, 3H), 2.20 (t, 2H), 2.75 (t, 2H), 2.9 (s, 3H), 3.07 (d, 2H), 4.06 (t, 2H), 4.1–4.25 (m, 1H), 6.61 (s, 2H), 6.76 (d, 2H), 6.9 (t, 1H), 6.92–6.98 (m, 2H), 7.05–7.15 (m, 2H), 7.20 (t, 2H), 12–14 (m, 2H).

EXAMPLE 9

1,2-Dimethyl-1-[1-[4-(4-methoxyphenoxy)butyl] piperidin-4-yl]-3-phenylisothiourea hydrogen fumarate (9)

9.1) 1-[4-(4-Methoxyphenoxy)butyl]-4-(methylamino) piperidine dihydrochloride (9.1)

The reductive amination of 6 g (21.6 mmol) of 1-[4-(4-methoxyphenoxy)butyl]-4-piperidone (prepared according to Ismaiel et al., *J. Med. Chem.*, 1993, 36, 2519–25) in the presence of 1.35 g (20 mmol) of methylamine hydrochloride and 4.6 g (21.6 mmol) of sodium triacetoxyborohydride according to the description of Example 3.1, makes it possible to prepare 5.3 g (Yd: 67%) of white powder of formula 9.1:

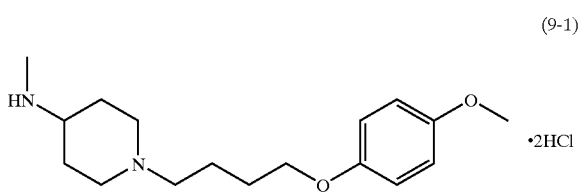

(9-1)

Empirical formula: $C_{17}H_{30}Cl_2N_2O_2$
Molecular mass: 365.34
White powder
NMR ($d_6$-DMSO) δ: 1.5–2.3 (m, 8H), 2.85–3.25 (m, 5H), 3.33 (s, 3H), 3.52–3.62 (m, 2H), 3.7 (s, 3H), 3.92 (d, 2H), 6.8–6.9 (m, 4H), 9.3–9.6 (m, 2H), 10.5–11 (m, 1H).

9.2) 1-Methyl-1-[1-[4-(4-methoxyphenoxy)butyl]piperidin-4-yl]-3-phenylthiourea (9.2)

The addition of 2.5 g (6.84 mmol) of the preceding compound 9.1 to 925 mg (6.84 mmol) of phenyl isothiocyanate according to the protocol of Example 1.1 gives 2.70 g (Yd: 92%) of the thiourea of formula 9.2:

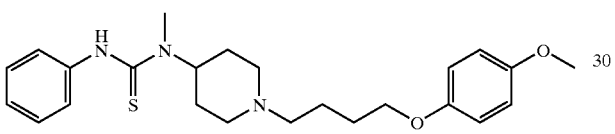

(9-2)

Empirical formula: $C_{24}H_{33}N_3O_2S$
Molecular mass: 427.58
Beige powder
Melting point: 111° C.
NMR (CDCl$_3$) δ: 1.65–2.7 (m, 12H), 3.06 (s, 3H), 3.06–3.25 (m, 2H), 3.77 (s, 3H), 3.93 (t,2H), 5.3 (m, 1H), 6.83 (s, 4H), 7.08 (s, 1H), 7.15–7.3 (m, 3H), 7.33 (t, 2H).

9.3) 1,2-Dimethyl-1-[1-[4-(4-methoxyphenoxy)butyl]piperidin-4-yl]-3-phenylisothiourea hydrogen fumarate (9)

The S-methylation of 1.5 g (3.5 mmol) of the preceding thiourea 9.2 with 240 μl of methyl iodide according to 1.2 results in the preparation of 690 mg (Yd: 35%) of the isothiourea of formula 9:

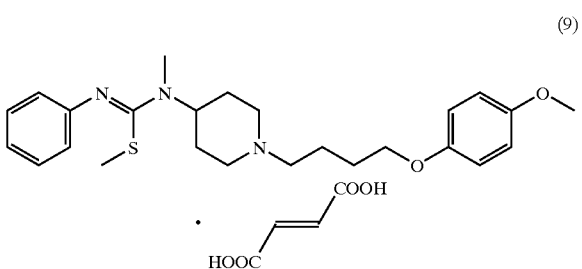

(9)

Empirical formula: $C_{29}H_{39}N_3O_6S$
Molecular mass: 557.689
White crystals
Melting point: 120° C.
NMR ($d_6$-DMSO) δ: 1.5–1.75 (m, 6H), 1.8–1.87 (m, 2H), 2 (s, 3H), 2.35–2.7 (m, 2H), 2.9 (s, 3H), 3.09 (d, 2H), 3.69 (s, 3H), 3.91 (t, 2H), 4.12–4.3 (m, 1H), 6.58 (s, 2H), 6.77 (d, 2H), 6.8–6.95 (m, 5H), 7.21 (t, 2H).

EXAMPLE 10

1,2-Dimethyl-1-(1-[4-(3,4-dimethylphenoxy)butyl] piperidin-4-yl]-3-phenylisothiourea hydrogen fumarate (10)

10.1) 1-[4-(3,4-Dimethylphenoxy)butyl]-4-(methylamino) piperidine dihydrochloride (10.1)

1,4-Dibromobutane, condensed with 3,4-dimethylphenol according to Ismaïel et al. (*J. Med. Chem.*, 1993, 36, 2519–25), gives 1-[4-bromobutoxy]-3,4-dimethylbenzene with a yield of 86%. The condensation of this compound (according to the same authors) with 1,4-dioxa-8-azaspiro[4.5]decane gives, after deprotection, 1-[4-(3,4-dimethylphenoxy)butyl]-4-piperidone in the form of an orangey oil with a yield of 61%. The reductive amination of this ketone (4.33 g or 15.7 mmol) with methylamine hydrochloride (1.06 g; 15.7 mmol) in the presence of sodium triacetoxyborohydride (4.33 g; 20.5 mmol) according to the protocol of Example 3.1 makes it possible to prepare 5.95 g (Yd: 63%) of the compound of formula 10:

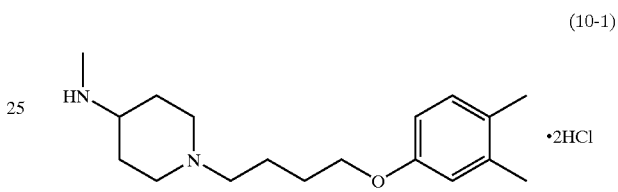

(10-1)

Empirical formula: $C_{18}H_{32}Cl_2N_2O$
Molecular mass: 362.37
White powder
Melting point: (decomp.) 195–198° C.
NMR ($d_6$-DMSO) δ: 1.5–2.1 (m, 6H), 2.13 (s, 3H), 2.18 (s, 3H), 2.18–2.3 (m, 2H), 2.8–3.2 (m, 4H), 3.33 (m, 3H), 3.4–3.7 (m, 2H), 3.93 (t, 2H), 6.6–6.7 (m, 1H), 6.73 (s, 1H), 7/02 (d, 1H), 9.3–9.7 (m, 2H), 10.5–11 (m, 1H).

10.2) 1-Methyl-1-[1-[4-(3,4-dimethylphenoxy)butyl] piperidin-4-yl]-3-phenylthiourea (10.2)

The application of the process of Example 1.1 to 2.69 g (7.4 mmol) of the preceding amine (10.1) and to 1 g (7.40 mmol) of phenyl isothiocyanate makes it possible to prepare 2.81 g (Yd: 89%) of the compound of formula 10.2:

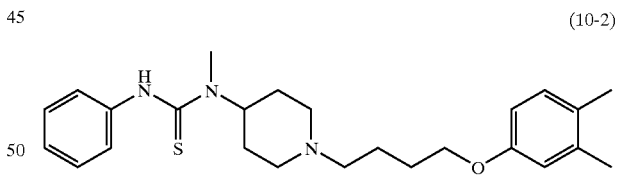

(10-2)

Empirical formula: $C_{25}H_{35}N_3OS$
Molecular mass: 425.61
Off-white powder
Melting point: 107° C.
NMR (CDCl$_3$) δ: 1.55–1.95 (m, 8H), 2.1–2.25 (m, 2H), 2.19 (s, 3H), 2.23 (s, 3H), 2.45 (t, 2H), 2.95–3.1 (m, 2H), 3.04 (s, 3H), 3.94 (t, 2H), 5.2 (m, 1H), 6.63 (dd, 1H), 6.7 (d, 1H), 7–7.06 (m, 2H), 7.1–7.27 (m, 3H), 7.36 (t, 2H).

10.3) 1,2-Dimethyl-1-[1-[4-(3,4-dimethylphenoxy)butyl] piperidin-4-yl]-3-phenylisothiourea hydrogen fumarate (10)

A solution of 1 g (2.35 mmol) of the preceding thiourea (10.2) in 10 ml of DMF is treated at 25° C. with 245 μl of dimethyl sulfate, stirred overnight at 25° C. and then heated for 1 h at 60° C. The mixture is evaporated to dryness and the residue is recovered in the usual way and purified by flash chromatography to give 325 mg (Yd: 32%) of a light yellow oil. This oil is taken up in ethanol and salified with a solution of 80 mg of fumaric acid in the same solvent to give 340 mg (Yd: 26%) of compound of formula:

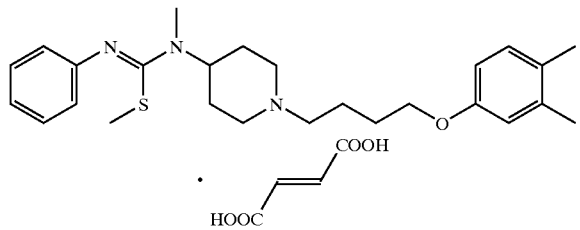

(10)

Empirical formula: $C_{30}H_{41}N_3O_5S$

Molecular mass: 555.72

White crystals

Melting point: 138–139° C.

NMR (d$_6$-DMSO) δ: 1.5–1.7 (m, 6H), 1.75–1.95 (m, 2H), 2 (s, 3H), 2.1–2.21 (m, 2H), 2.12 (s, 3H), 2.2 (s, 3H), 2.4–2.6 (m, 2H), 2.89 (s, 3H), 3.02–3.2 (m, 2H), 3.92 (t, 2H), 4.1–4.3 (m, 1H), 6.58 (s, 2H), 6.63 (dd, 1H), 6.7–6.8 (m, 3H), 6.9 (t, 1H), 7 (d, 1H), 7.2 (t, 2H).

EXAMPLE 11

1,2-Dimethyl-1-[1-[4-(2-methoxy-4-chlorophenoxy) butyl]piperidin-4-yl]-3-phenylisothiourea hydrogen fumarate (11)

11.1) 1-[4-(2-Methoxy-4-chlorophenoxy)butyl]-4-(methylamino)piperidine dihydrochloride (11.1)

The condensation of 1,4-dibromobutane with 2-methoxy-4-chlorophenol gives, according to Ismaiel et al., 1-(4-bromobutoxy)-2-methoxy-4-chlorobenzene with a yield of 86%. The alkylation of 1,4-dioxa-8-azaspiro[4.5]decane by this derivative provides, after deprotection, 1-[4-(2-methoxy-4-chlorophenoxy)butyl]-4-piperidone with a yield of 96%. The reductive amination of 4.7 g (~15 mmol) of the preceding ketone with methylamine hydrochloride (1.02 g) in the presence of 4.15 g (19 mmol) of sodium triacetoxyborohydride according to Example 3.1 gives 3.92 g (Yd: 65%) of compound 11.1 of formula:

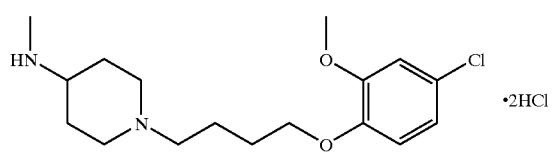

(11-1)

Empirical formula: $C_{17}H_{29}Cl_3N_2O_2$

Molecular mass: 399.79

Light yellow powder

NMR (d$_6$-DMSO) δ: 1.5–2.27 (m, 8H), 2.51 (s, 3H), 2.8–3.25 (m, 5H), 3.4–3.6 (m, 2H), 3.8 (s, 3H), 3.97 (t, 2H), 6.92 (dd, 1H), 6.96–6.99 (m, 1H), 7.02 (d, 1H), 9.3–9.7 (m, 2H), 10.2–11.1 (m, 1H).

11.2) 1-Methyl-1-[1-[4-(2-methoxy-4-chlorophenoxy) butyl]piperidin-4-yl]-3-phenylthiourea (11.2)

The application of the procedure of 1.1 to 2.85 g (7.13 mmol) of the preceding diamine 11.1 results in the formation of 2.98 g (Yd: 90%) of the thiourea of formula 11.2:

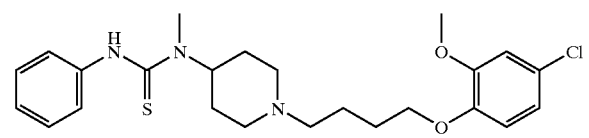

(11-2)

Empirical formula: $C_{24}H_{32}ClN_3O_2S$

Molecular mass: 462.04

Light beige crystals

Melting point: 129° C.

NMR (CDCl$_3$) δ: 1.5–2.1 (m, 8H), 2.1–2.3 (m, 2H), 2.35–2.6 (m, 2H), 3.04 (s, 3H), 3–3.2 (m, 2H), 3.85 (s, 3H), 4.01 (t, 2H), 5.24 (m, 1H), 6.78 (d, 1H), 6.8–6.9 (m, 2H), 7.06 (s, 1H), 7.1–7.29 (m, 3H), 7.35 (t, 2H).

11.3) 1,2-Dimethyl-1-[1-[4-(2-methoxy-4-chlorophenoxy) butyl]piperidin-4-yl]-3-phenylisothiourea hydrogen fumarate (11)

The S-methylation of 1.2 g (2.6 mmol) of the preceding thiourea 11.2 according to the process of Example 1.2 gives 618 mg (Yd: 40%) of the derivative of formula 11:

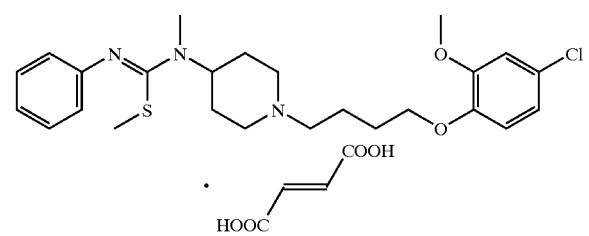

(11)

Empirical formula: $C_{29}H_{38}ClN_3O_6S$

Molecular mass: 592.13

Off-white crystals

Melting point: 106–107° C.

NMR (d$_6$ DMSO) δ: 1.5–1.82 (m, 6H), 1.84–1.97 (m, 2H), 2 (s, 3H), 2.35 (t, 2H), 2.61 (t, 2H), 2.96 (s, 3H), 3.16 (d, 2H), 3.94 (s, 3H), 3.96 (t, 2H), 4.15–4.35 (m, 1H), 6.59 (s, 2H), 6.76 (d, 2H), 6.8–7.1 (m, 4H), 7.21 (t, 2H), 12–14 (m, 2H).

EXAMPLE 12

1,2-Dimethyl-1-[1-[4-(3,4-difluorophenoxy)butyl] piperidin-4-yl]-3-(2-fluorophenyl)isothiourea hydrogen fumarate (12)

12.1) 1-Methyl-1-[1-[4-(3,4-difluorophenoxy)butyl] piperidin-4-yl]-3-(2-fluorophenyl)thiourea (12.1)

The application of the protocol of Example 1.1 to 610 mg (4 mmol) of 2-fluorophenyl isothiocyanate and 1.20 g (4 mmol) of 1-[4-(3,4-difluorophenoxy)butyl]-4-

(methylamino)piperidine gives 1.65 g (Yd: 91%) of white crystals of formula 12.1:

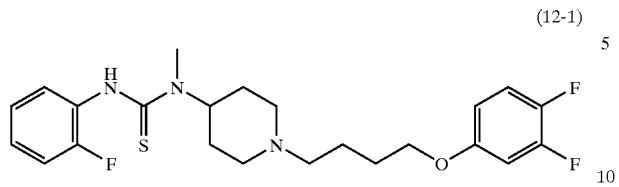

(12-1)

Empirical formula: $C_{23}H_{28}F_3N_3OS$
Molecular mass: 451.54
White crystals
Melting point: 126° C.
NMR (CDCl$_3$) δ: 1.5–1.95 (m, 8H), 2.13 (t, 2H), 2.42 (t, 2H), 3–3.06 (m, 2H), 3.11 (s, 3H), 3.94 (t, 2H), 5.21 (m, 1H), 6.5–6.6 (m, 1H), 6.5–6.75 (m, 1H), 6.92 (s, 1H), 6.8–7.3 (m, 4H), 7.75–8.01 (m, 1H).

12.2) 1,2-Dimethyl-1-[1-[4-(3,4-difluorophenoxy)butyl] piperidin-4-yl]-3-(2-fluorophenyl)isothiourea hydrogen fumarate (12)

200 mg (3.54 mmol) of CaO and 242 μl (3.9 mmol) of methyl iodide are added to a solution of 1.60 g (3.54 mmol) of the preceding thiourea 12.1 in 20 ml of chloroform and then the mixture is brought to reflux for 3 hours. The mixture is filtered, then washed with water and with aqueous saline solution, and dried on anhydrous sodium sulfate. After removing the inorganic salt, the filtrate is evaporated to dryness and purified by flash chromatography, elution being carried out with a 95/4.5/0.5 CHCl$_3$/MeOH/NH$_4$OH mixture. 1.1 g of oil are recovered, which oil is salified in the usual way to give 790 mg (Yd: 39%) of the compound of formula 12:

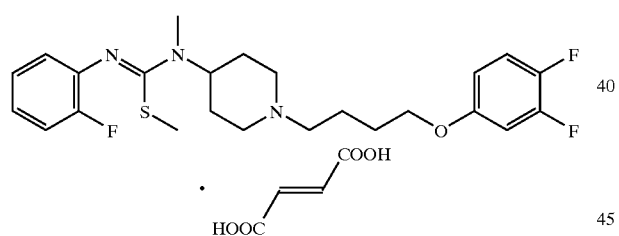

(12)

Empirical formula: $C_{28}H_{34}F_3N_3O_5S$
Molecular mass: 581.64
White crystals
Melting point: 148° C.
NMR (d$_6$-DMSO) δ: 1.5–1.75 (m, 6H), 1.78–1.9 (m, 2H), 2.08 (s, 3H), 2.15 (t, 2H), 2.41–2.6 (m, 2H), 2.93 (s, 3H), 3.01–3.09 (m, 2H), 3.97 (t, 2H), 4.13–4.25 (m, 1H), 6.58 (s, 2H), 6.72–6.79 (m, 1H), 6.81–6.87 (m, 1H), 6.9–6.95 (m, 1H), 7.0–7.1 (m, 3H), 7.33 (q, 1H), 12–14 (m, 2H).

EXAMPLE 13

1,2-Dimethyl-1-[1-[4-(3,4-difluorophenoxy)butyl] piperidin-4-yl]-3-(4-fluorophenyl)isothiourea hydrogen fumarate (13)

13.1) 1-Methyl-1-[1-[4-(3,4-difluorophenoxy)butyl] piperidin-4-yl]-3-(4-fluorophenyl)thiourea (13.1)

The condensation of 1.2 g (4 mmol) of 1-[4-(3,4-difluorophenoxy)butyl]-4-(methylamino)piperidine with 0.61 g (4 mmol) of 4-fluorophenyl isothiocyanate in THF according to the protocol of Example 1.1 gives 1.75 g (Yd: 95%) of a powder of formula 13.1

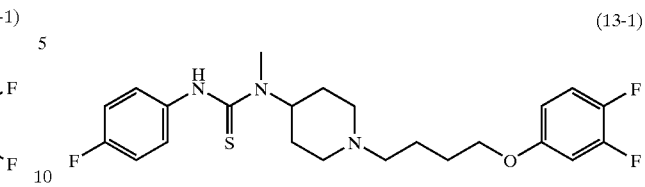

(13-1)

Empirical formula: $C_{23}H_{28}F_3N_3OS$
Molecular mass: 451.54
White powder
Melting point: 133° C.
NMR (CDCl$_3$) δ: 1.5–1.9 (m, 8H), 2.13 (t, 2H), 2.42 (t, 2H), 3–3.1 (m, 2H), 3.06 (s, 3H), 3.92 (t, 2H), 5.23 (m, 1H), 6.5–6.6 (m, 1H), 6.65–6.67 (m, 1H), 6.94 (s, 1H), 7–7.08 (m, 3H), 7.2–7.3 (m, 2H).

13.2) 1,2-Dimethyl-1-[1-[4-(3,4-difluorophenoxy)butyl] piperidin-4-yl]-3-(4-fluorophenyl)isothiourea hydrogen fumarate (13)

The isothiourea 13 is prepared according to Example 1.2 with a yield of 21% by S-methylation of 1.2 g (2.65 mmol) of the preceding thiourea 13.1.

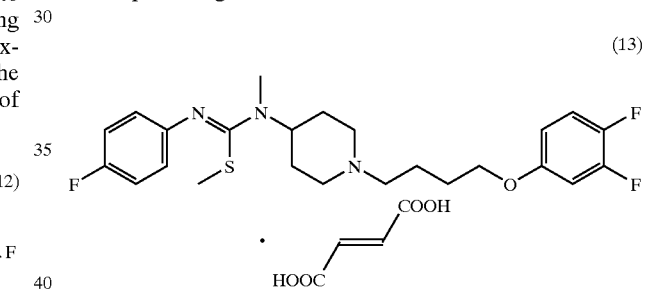

(13)

Empirical formula: $C_{28}H_{34}F_3N_3O_5S$
Molecular mass: 581.64
White crystals
Melting point: 125° C.
NMR (d$_6$-DMSO) δ: 1.5–1.73 (m, 6H), 1.74–1.9 (m, 2H), 2.02 (s, 3H), 2.15 (t, 2H), 2.4–2.6 (m, 2H), 2.89 (s, 3H), 3–3.1 (m, 2H), 3.97 (t, 2H), 4.1–4.25 (m, 1H), 6.5 (s, 2H), 6.7–6.8 (m, 3H), 6.95–7.1 (m, 3H), 7.25–7.4 (m, 1H), 11–13 (m, 2H).

EXAMPLE 14

1,2-Dimethyl-1-[1-[4-(3,4-difluorophenoxy)butyl] piperidin-4-yl]-3-(4-chlorophenyl)isothiourea hydrogen fumarate (14)

14.1) 1-Methyl-1-[1-[4-(3,4-difluorophenoxy)butyl] piperidin-4-yl]-3-(4-chlorophenyl)thiourea (14.1)

By starting from 0.85 g (5 mmol) of 4-chlorophenyl isothiocyanate and 1.5 g (5 mmol) of 1-[4-(3,4-difluorophenoxy)butyl]-4-(methylamino)piperidine in 30 ml of THF, 2.16 g (Yd: 92%) of compound 14.1 is prepared according to the process of Example 1.1, compound 14.1 having the formula:

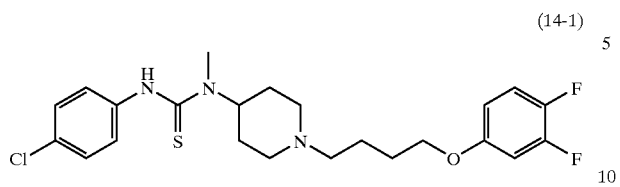

(14-1)

Empirical formula: $C_{23}H_{28}ClF_2N_3OS$

Molecular mass: 467.99

Off-white crystals

Melting point: 149° C.

(Melting point of the hydrogen fumarate: 166° C.)

NMR (CDCl$_3$) δ: 1.5–2 (m, 8H), 2.14 (t, 2H), 2.43 (t, 2H), 3–3.1 (m, 2H), 3.06 (s, 3H), 3.92 (t, 2H), 5.12 (m, 1H), 6.5–6.6 (m, 1H), 6.62–6.75 (m, 1H), 6.95 (s, 1H), 7–7.08 (m, 1H), 7.22 (d, 2H), 7.31 (d, 2H).

14.2) 1,2-Dimethyl-1-[1-[4-(3,4-difluorophenoxybutyl] piperidin-4-yl]-3-(4-chlorophenyl)isothiourea hydrogen fumarate (14)

By using the process of Example 1.2, by heating a mixture of 1.65 g (3.5 mmol) of the preceding thiourea 14.1 and 240 μl of methyl iodide (3.85 mmol) in 30 ml of ethanol at 40° C. for 2 h, the compound 14 is prepared with a yield of 36%, the compound 14 having the formula:

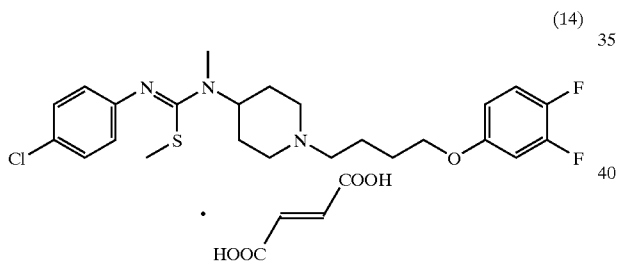

(14)

Empirical formula: $C_{28}H_{34}ClF_2N_3O_5S$

Molecular mass: 598.09

Pulverulent white crystals

Melting point: 130° C.

NMR (d$_6$-DMSO) δ: 1.5–1.75 (m, 6H), 1.77–1.9 (m, 2H), 2.03 (s, 3H), 2.18 (t, 2H), 2.4–2.6 (m, 2H), 2.9 (s, 3H), 3.07 (d, 2H), 3.97 (t, 22H), 4.1–4.2 (m, 1H), 6.58 (s, 2H), 6.7–6.8 (m, 3H), 7–7.09 (m, 1H), 7.2–7.3 (m, 2H), 7.3–7.4 (m, 1H).

EXAMPLE 15

1,2-Dimethyl-1-[1-[4-(3,4-difluorophenoxy)butyl] piperidin-4-yl]-3-(4-methylphenyl)isothiourea hydrogen fumarate (15)

15.1) 1-Methyl-1-[1-[4-(3,4-difluorophenoxy)butyl] piperidin-4-yl]-3-(4-methylphenyl)thiourea (15.1)

The replacement of phenyl isothiocyanate by para-tolyl isothiocyanate (0.60 g; 4 mmol) in the procedure of Example 1.1 with THF as solvent results, with a yield of 95%, in the thiourea 15.1 of formula:

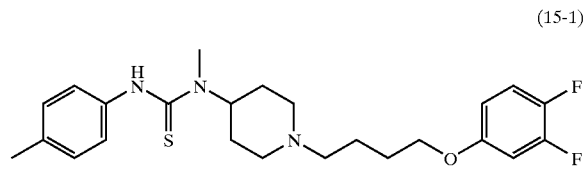

(15-1)

Empirical formula: $C_{24}H_{31}F_2N_3OS$

Molecular mass: 447.57

Off-white crystals

Melting point: 151° C.

NMR (CDCl$_3$) δ: 1.5–1.95 (m, 8H), 2.13 (t, 2H), 2.33 (s, 3H), 2.42 (t, 2H), 2.95–3.1 (m, 5H), 3.92 (t, 2H), 5.21 (m, 1H), 6.5–6.6 (m, 1H), 6.65–6.8 (m, 1H), 6.98 (s, 1H), 7–71 (m, 1H), 7.1–7.17 (m, 4H).

15.2) 1,2-Dimethyl-1-[1-[4-(3,4-difluorophenoxy)butyl] piperidin-4-yl]-3-(4-methylphenyl)isothiourea hydrogen fumarate (15)

830 mg (Yd: 57%) of crystals of formula 15 are prepared by S-methylation of 1.12 g (2.5 mmol) of the preceding thiourea 15.1 according to the process of Example 1.2:

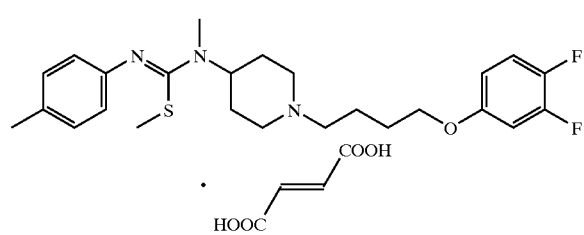

(15)

Empirical formula: $C_{29}H_{37}F_2N_3O_5S$

Molecular mass: 577.67

White crystals

Melting point: 141° C.

NMR (d$_6$-DMSO) δ: 1.5–1.75 (m, 6H), 1.8–1.9 (m, 2H), 2 (s, 3H), 2.18 (t, 2H), 2.23 (s, 3H), 2.42–2.55 (m, 2H), 2.87 (s, 3H), 3.07 (d, 2H), 3.97 (t, 2H), 4.1–4.25 (m, 1H), 6.58 (s, 2H), 6.64 (d, 2H), 6.7–6.8 (m, 1H), 7.01 (d, 2H), 7.02–7.09 (m, 1H), 7.33 (q, 1H).

EXAMPLE 16

1,2-Dimethyl-1-[1-[4-(3,4-difluorophenoxy)butyl] piperidin-4-yl]-3-(4-methoxyphenyl)isothiourea hydrogen fumarate (16)

16.1) 1-Methyl-1-[1-[4-(3,4-difluorophenoxy)butyl] piperidin-4-yl]-3-(4-methoxyphenyl)thiourea (16.1)

By using the protocol of Example 1.1 with 4-methoxyphenyl isothiocyanate (660 mg: 4 mmol) as acylating agent in THF, 1.66 g (Yd: 90%) of compound 16.1 are prepared, compound 16.1 having the formula:

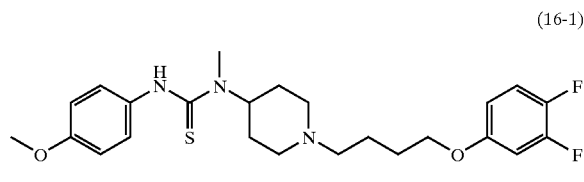

(16-1)

Empirical formula: $C_{24}H_{31}F_2N_3O_2S$

Molecular mass: 463.57

Beige powder

Melting point: 122° C.

NMR (CDCl$_3$) δ: 1.5–1.9 (m, 8H), 2.14 (t, 2H), 2.42 (t, 2H), 2.95–3.12 (m, 2H), 3.05 (s, 3H), 3.81 (s, 3H), 3.92 (t, 2H), 5.24 (m, 1H), 6.5–6.6 (m, 1H), 6.65–6.75 (m, 1H), 6.88 (d, 2H), 6.94(s, 1H), 7–7.08 (m, 1H), 7.17 (d, 2H).

16.2) 1,2-Dimethyl-1-[1-[4-(3,4-difluorophenoxy)butyl]piperidin-4-yl]-3-(4-methoxyphenyl)isothiourea hydrogen fumarate (16)

The S-alkylation carried out on 1.15 g (2.5 mmol) of the thiourea 16.1 according to the process of Example 1.2 gives 692 mg (Yd: 46%) of the isothiourea of formula 16:

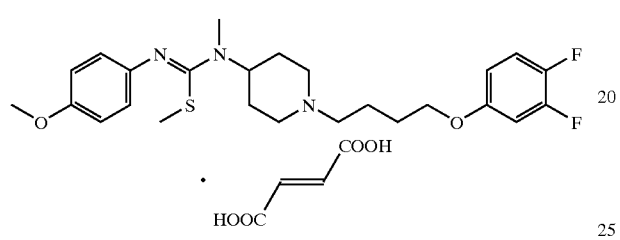

(16)

Empirical formula: C$_{29}$H$_{37}$F$_2$N$_3$O$_6$S

Molecular mass: 593.67

White crystals

Melting point: 130° C.

NMR (d$_6$-DMSO) δ: 1.4–1.9 (m, 8H), 2 (s, 3H), 2.18 (t, 2H), 2.4–2.6 (m, 2H), 2.87 (s, 3H), 3.07 (d, 2H), 3.7 (s, 3H), 3.97 (t, 2H), 4.1–4.25 (m, 1H), 6.58 (s, 2H), 6.69 (d, 2H), 6.72–6.85 (m, 3H), 7–7.1 (m, 1H), 7.33 (q, 1H).

EXAMPLE 17

1,2-Dimethyl-1-[1-[4-(3,4-difluorophenoxy)butyl]piperidin-4-yl]-3-(2,6-dimethylphenyl)isothiourea hydrogen fumarate (17)

17.1) 1-Methyl-1-[1-[4-(3,4-difluorophenoxy)butyl]piperidin-4-yl]-3-(2,6-dimethylphenyl)thiourea (17.1)

The use of 820 mg (5 mmol) of 2,6-dimethylphenyl isothiocyanate in the protocol of Example 1.1 results in the formation of 1.96 g (Yd 86%) of the thiourea of formula 17.1

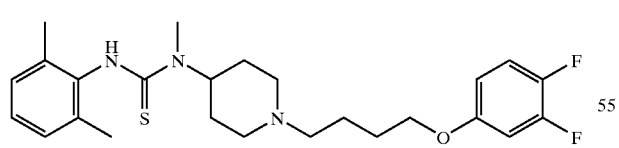

(17-1)

Empirical formula: C$_{25}$H$_{33}$F$_2$N$_3$OS

Molecular mass: 461.60

Off-white powder

Melting point: 114° C.

NMR (CDCl$_3$) δ: 1.5–1.9 (m, 8H), 2.07–2.18 (m, 2H), 2.24 (s, 6H), 2.32–2.5 (m, 2H), 3–3.05 (m, 2H), 3.09 (s, 3H), 3.92 (t, 2H), 5.24 (m, 1H), 6.5–6.63 (m, 1H), 6.66–6.74 (m, 1H), 6.95–7.2 (m, 4H).

17.2) 1,2-Dimethyl-1-[1-[4-(3,4-difluorophenoxy)butyl]piperidin-4-yl]-3-(2,6-dimethylphenyl)isothiourea hydrogen fumarate (17)

The preceding thiourea 17.1 (1.33 g; 2.88 mmol) is treated according to the process of 1.2 to give 720 mg (Yd: 42%) of the isothiourea of formula 17:

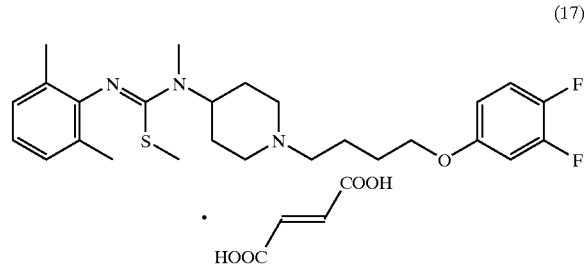

(17)

Empirical formula: C$_{30}$H$_{39}$F$_2$N$_3$O$_5$S

Molecular mass: 591.70

Off-white crystals

Melting point: 129° C.

NMR (d$_6$-DMSO) δ: 1.5–1.8 (m, 6H), 1.8–1.92 (m, 2H), 1.97 (s, 6H), 2.11 (s, 3H), 2.19 (t, 2H), 2.4–2.55 (m, 2H), 2.87 (s, 3H), 3.05–3.13 (m, 2H), 3.9–4.08 (m, 3H), 6.58 (s, 2H), 6.7–6.8 (m, 2H), 6.94 (d, 2H), 7–7.1 (m, 1H), 7.33 (q, 1H).

EXAMPLE 18

1,2-Dimethyl-1-[1-[4-(3,4-difluorophenoxy)butyl]piperidin-4-yl]-3-[2,6-diisopropylphenyl]isothiourea hydrogen fumarate (18)

18.1) 1-Methyl-1-[1-[4-(3,4-difluorophenoxy)butyl]piperidin-4-yl]-3-[2,6-diisopropylphenyl]thiourea (18.1)

2.31 g (Yd: 89%) of the thiourea of formula 18.1 are prepared from 1.10 g (5 mmol) of 2,6-diisopropylphenyl isothiocyanate in 20 ml of THF according to the protocol of 1.1:

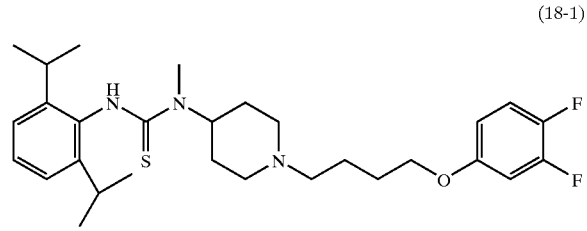

(18-1)

Empirical formula: C$_{29}$H$_{41}$F$_2$N$_3$OS

Molecular mass: 517.70

Off-white powder

Melting point: 130° C. (Hydrogen fumarate: M.p.=164° C.)

NMR (CDCl$_3$) δ: 1.16 (d, 6H), 1.29 (d, 6H), 1.45–1.95 (m, 8H), 2–2.25 (m, 2H), 2.3–2.5 (m, 2H), 3.03 (t, 2H), 3.14 (s, 3H), 3.93 (t, 2H), 6.47–6.62 (m, 2H), 6.65–6.75 (m, 1H), 7.05 (q, 1H), 7.19 (d, 2H), 7.26–7.4 (m, 1H).

18.2) 1,2-Dimethyl-1-[1-[4-(3,4-difluorophenoxy)butyl]piperidin-4-yl]-3-[2,6-diisopropylphenyl]isothiourea hydrogen fumarate (18)

The S-methylation of 1.50 g (2.9 mmol) of the preceding thiourea 18.1 results, by heating for 4 h at 50° according to Example 14.2, in the preparation of 698 mg (Yd: 37%) of the corresponding S-methyl isothiourea 18:

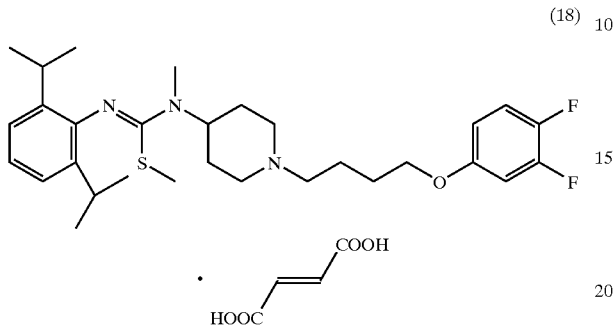

(18)

Empirical formula: $C_{34}H_{47}F_2N_3O_5S$

Molecular mass: 642.82

Off-white powder

Melting point 194° C.

NMR ($d_6$-DMSO) δ: 1.05 (d, 6H), 1.13 (d, 6H), 1.6–1.85 (m, 6H), 1.9–2.1 (m, 2H), 2.18 (s, 3H), 2.7–3 (m, 4H), 2.89 (s, 3H), 3.1–3.7 (m, 4H), 4 (t, 2H), 4.04–4.3 (m, 1H), 6.62 (s, 2H), 6.7–6.8 (m, 1H), 6.91 (t, 1H), 6.96–7.12 (m, 3H), 7.35 (q, 1H), 11–13 (m, 2H).

EXAMPLE 19

1,2-Dimethyl-1-[1-[4-(3,4-difluorophenoxy)butyl]piperidin-4-yl]-3-(3-fluorophenyl)isothiourea hydrogen fumarate (19)

19.1) 1-Methyl-1-[1-[4-(3,4-difluorophenoxy)butyl]piperidin-4-yl]-3-(3-fluorophenyl)thiourea (19.1)

The application of the protocol of Example 1.1 to 0.61 g (4 mmol) of 3-fluorophenyl isothiocyanate makes it possible to prepare 1.87 g (Yd: 94%) of white powder of formula 19.1:

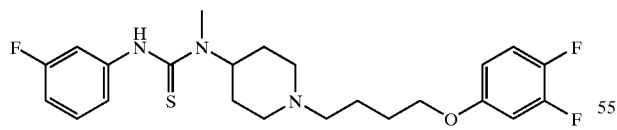

(19-1)

Empirical formula: $C_{23}H_{28}F_3N_3OS$

Molecular mass: 451.84

White powder

Melting point: 128° C.

NMR (CDCl$_3$) δ: 1.5–1.9 (m, 8H), 2.13 (s, 2H), 2.35–2.48 (m, 2H), 2.95–3 (m, 2H), 3.04 (s, 3H), 3.92 (t, 2H), 5.16 (m, 1H), 6.5–6.6 (m, 1H), 6.65–6.72 (m, 1H), 6.88 (m, 1H), 6.95–7.1 (m, 4H), 7.23–7.4 (m, 1H).

19.2) 1,2-Dimethyl-1-[1-(4-(3,4-difluorophenoxy)butyl]piperidin-4-yl]-3-(3-fluorophenyl)isothiourea hydrogen fumarate (19)

The S-methylation of 1.60 g (3.54 mmol) of the thiourea 19.1 gives 880 mg (Yd: 42%) of the compound of formula 19:

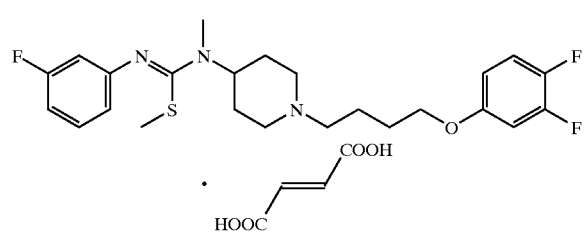

(19)

Empirical formula: $C_{28}H_{34}F_3N_3O_6S$

Molecular mass: 581.64

White crystals

Melting point: 133° C.

NMR ($d_6$-DMSO) δ: 1.5–1.9 (m, 8H), 2.03 (s, 3H), 2.14 (t, 2H), 2.46 (t, 2H), 2.9 (s, 3H), 3.05 (d, 2H), 3.97 (t, 2H), 4.12–4.25 (m, 1H), 6.5–6.63 (m, 4H), 6.67–6.8 (m, 2H), 7–7.1 (m, 1H), 7.23 (q, 1H), 7.33 (q, 1H).

EXAMPLE 20

1,2-Dimethyl-1-[1-[4-(3,4-difluorophenoxy)butyl]piperidin-4-yl]-3-(4-nitrophenyl)isothiourea hydrogen fumarate (20)

20.1) 1-Methyl-1-[1-[4-(3,4-difluorophenoxy)butyl]piperidin-4-yl]-3-(4-nitrophenyl)thiourea (20.1)

By condensation of 0.72 g (4 mmol) of 4-nitrophenyl isothiocyanate according to Example 1.1, 1.71 g (Yd: 88%) of yellow powder of formula 20.1 are prepared:

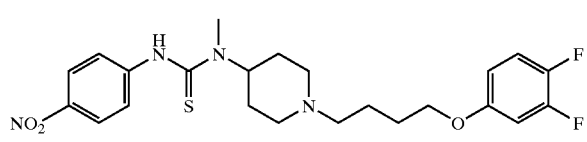

(20-1)

Empirical formula: $C_{23}H_{28}F_2N_4O_3S$

Molecular mass: 478.55

Pulverulent yellow crystals

Melting point: 108° C.

NMR (CDCl$_3$) δ: 1.5–1.95 (m, 8H), 2.14 (t, 2H), 2.35–2.5 (m, 2H), 3–3.15 (m, 2H), 3.11 (s, 3H), 3.93 (t, 2H), 5.15 (m, 1H), 6.52–6.62 (m, 1H), 6.65–6.78 (m, 1H), 7.05 (q, 1H), 7.16 (s, 1H), 7.45 (d, 2H), 8.2 (d, 2H).

20.2) 1,2-Dimethyl-1-[1-[4-(3,4-difluorophenoxy)butyl]piperidin-4-yl]-3-(4-nitrophenyl)isothiourea hydrogen fumarate (20)

The S-methylation of 1.60 g (3.34 mmol) of the preceding thiourea 20.1 according to Example 12.2 makes it possible to prepare 610 mg (Yd: 30%) of the isothiourea of formula 20:

(20)

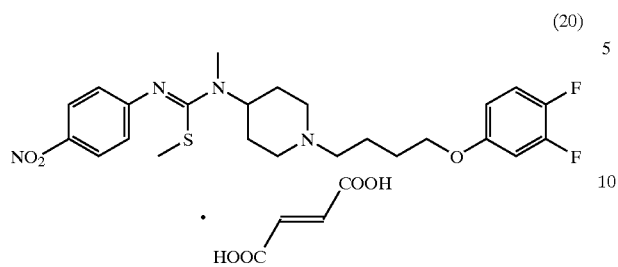

Empirical formula: $C_{28}H_{34}F_2N_4O_7S$
Molecular mass: 608.64
Yellow crystals
Melting point: 132° C.
NMR ($d_6$-DMSO) δ: 1.5–1.74 (m, 6H), 1.75–1.90 (m, 2H), 2.03 (s, 3H), 2.1 (t, 2H), 2.46 (t, 2H), 3.05 (s, 3H), 3.1 (d, 2H), 3.97 (t, 2H), 4.2–4.3 (m, 1H), 6.59 (s, 2H), 6.74–6.78 (m, 1H), 6.95 (d, 2H), 7–7.1 (m, 1H), 7.33 (q, 1H), 8.09 (d, 2H), 12–14 (m, 2H).

EXAMPLE 21

1,2-Dimethyl-1-[1-[4-(3,4-difluorophenoxy)butyl]piperidin-4-yl]-3-(2,6-difluorophenyl)isothiourea hydrogen fumarate (21)

21.1) 1-Methyl-1-[1-[4-(3,4-difluorophenoxy)butyl]piperidin-4-yl]-3-(2,6-difluorophenyl)thiourea (21.1)

The reaction of 1 g (5.84 mmol) of 2,6-difluorophenyl isothiocyanate according to the description of Example 1.1 gives 2.88 g (Yd: 81%) of white powder of formula 21.1:

(21-1)

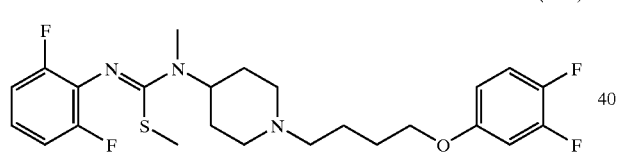

Empirical formula: $C_{23}H_{27}F_4N_3OS$
Molecular mass: 469.53
Pulverulent white crystals
Melting point: 120° C.
NMR (CDCl$_3$) δ: 1.5–2 (m, 8H), 2.15 (t, 2H), 2.43 (t, 2H), 3–3.1 (m, 2H), 3.15 (s, 3H), 3.92 (t, 2H), 5.19 (m, 1H), 6.39 (s, 1H), 6.5–6.6 (m, 1H), 6.65–6.75 (m, 1H), 6.97 (t, 2H), 7.05 (q, 1H), 7.2–7.6 (m, 1H).

21.2) 1,2-Dimethyl-1-[1-[4-(3,4-difluorophenoxy)butyl]piperidin-4-yl]-3-(2,6-difluorophenyl)isothiourea hydrogen fumarate (21)

The reaction of 0.60 g (4.2 mmol) of methyl iodide with 1.88 g (4 mmol) of the preceding thiourea 21.1 in 10 ml of DMF according to the protocol of 1.2 makes it possible to prepare 690 mg (Yd: 29%) of the isothiourea 21 of formula:

(21)

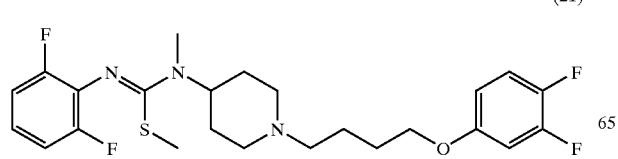

-continued

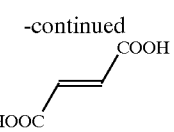

Empirical formula: $C_{28}H_{33}F_4N_3O_5S$
Moleculare mass: [lacuna]
White crystals
NMR ($d_6$-DMSO) δ: 1.6–2.1 (m, 8H), 2.17 (s, 3H), 2.7–2.95 (m, 4H), 3 (s, 3H), 3.35–3.45 (m, 2H), 3.99 (t, 2H), 4.3–4.5 (m, 1H), 6.62 (s, 2H), 6.7–6.8 (m, 1H), 6.9–7.12 (m, 4H), 7.35 (q, 1H), 11–13 (m, 2H).

EXAMPLE 22

1,2-Dimethyl-1-[1-[3-[2-(4-fluorophenyl)ethoxy]propyl]piperidin-4-yl]-3-phenylisothiourea hydrogen fumarate (22)

22.1) 4-Fluoro-1-[2-(3-chloropropoxy)ethyl]benzene (22.1)

A solution of 86 g (2.14 mol) of NaOH pellets in 86 g of water is stirred, cooled to 25° C. and then treated with 20 g (0.143 mol) of 4-fluorophenethyl alcohol, 113 ml (1.14 mol) of 1-bromo-3-chloropropane and then with 4.85 g (14 mmol) of tetrabutylammonium hydrogen sulfate. Vigorous stirring is maintained for 4 h at 25° C., extraction is then carried out with ether and the extract is washed with water and with aqueous saline solution and dried over anhydrous sodium sulfate. After removing the inorganic salt, the filtrate is evaporated to dryness and the residual oil is rectified under vacuum to give 20.3 g (Yd: 65%) of product of formula 22.1:

(22-1)

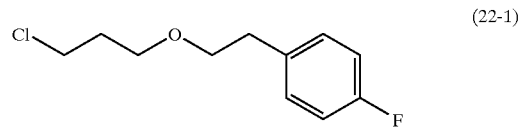

Empirical formula: $C_{11}H_{14}ClFO$

Molecular mass: 216.67

Colorless oil

Boiling point: 94–97° C./0.4 mbar.

NMR (CDCl$_3$) δ: 2.08 (q, 2H), 2.85 (t, 2H), 3.46 (t, 2H), 3.55 (t, 2H), 3.63 (t, 2H), 6.97 (t, 2H), 7.1–7.2 (m, 2H).

22.2) 1-[3-[2-(4-Fluorophenyl)ethoxy]propyl]-4-piperidone (22.2)

A solution of 17.5 g (81 mmol) of 1-fluoro-4-[2-(3-chloropropyloxy)ethyl]benzene (22.1) in 175 ml of DMF is treated while stirring at 25° C. with 10.4 ml of 1,4-dioxa-8-azaspiro[4.5]decane (11.6 g or 81 mmol) and 12.4 g (85 mmol) of a milled mixture of 98/02 K$_2$CO$_3$/KI and then the mixture is heated at 80° C. for 5 h. The insoluble material is removed by filtration and the solution obtained is evaporated to dryness under vacuum. The residue is mainly composed of the protected aminoketone of formula 22.2.1, which is not isolated.

(22-2-1)

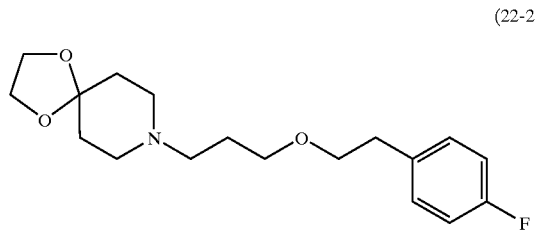

This compound is treated with 160 ml of 6N hydrochloric acid and heated at 100° for 2 h with stirring. After returning to 25°, the materials which cannot be converted to salts are extracted with $CH_2Cl_2$ and the aqueous phase is separated, cooled to 0° and basified with 10N sodium hydroxide to pH 12–13. The expected aminoketone is extracted with $CH_2Cl_2$ and then the extract is washed with water and with aqueous saline solution, dried over anhydrous sodium sulfate, filtered and evaporated to dryness: 17.3 g (Yd: 76%) of crude residue of formula 22.2 are obtained:

(22-2)

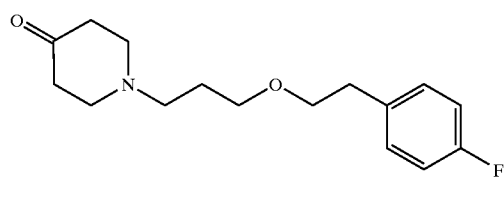

Empirical formula: $C_{16}H_{22}FNO_2$

Molecular mass: 279.35

Slightly orangey viscous oil

NMR ($CDCl_3$) δ: 1.5–1.85 (m, 2H), 2.36–2.58 (m, 6H), 2.72 (t, 4H), 2.85 (t, 2H), 3.5 (t, 2H), 3.61 (t, 2H), 6.91–7 (m, 2H), 7.1–7.2 (m, 2H).

22.3) 4-Methylamino-1-[3-[2-(4-fluorophenyl)ethoxy]propyl]piperidine dihydrochloride (22.3)

A solution of 14.7 g (52.6 mmol) of the preceding ketoamine (22.2) in 150 ml of $CH_2Cl_2$ is treated with 3.5 g (52.6 mmol) of methylamine hydrochloride and then methanol is added until dissolution is complete. After stirring for 3 h at 25° C., the mixture is cooled on an ice bath and 14.5 g (68.5 mmol) of sodium triacetoxyborohydride are added portionwise and, finally, 3 ml of acetic acid are added dropwise. Stirring is continued overnight at 25° C. The reaction mixture is poured into ice and basified to pH 12–13. The base released is extracted in the usual way to give a greenish oil.

After dissolution in 70 ml of absolute ethanol and treatment at 0° C. with a 2.5N ethanolic hydrochloric acid solution, the salt crystallizes after initiation and is recovered by filtration to give 13.6 g (Yd: 70%) of crystals of formula 22.3:

(22-3)

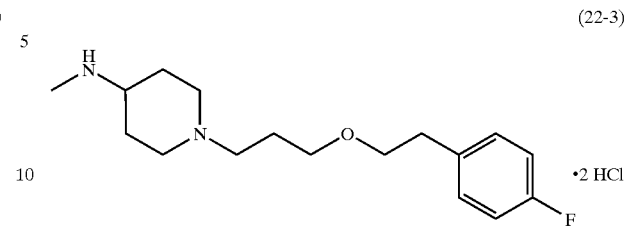

Empirical formula: $C_{17}H_{29}Cl_2FN_2O$

Molecular mass: 367.34

Off-white crystals

NMR ($d_6$-DMSO) δ: 1.9–2.04 (m, 4H), 2.08–2.28 (m, 2H), 2.5 (s, 3H), 2.8 (t, 2H), 2.85–3.1 (m, 4H), 3.17 (m, 1H), 3.45 (t, 2H), 3.5–3.6 (m, 4H), 7.11 (t, 2H), 7.25–7.32 (m, 2H), 9.3–9.7 (m, 2H), 10.6–11.08 (m, 1H).

22.4) 1-[1-[3-[2-(4-Fluorophenyl)ethoxy]propyl]piperidin-4-yl]-1-methyl-3-phenylthiourea (22.4)

A solution of 736 mg (5.44 mmol) of phenyl isothiocyanate in 15 ml of ethanol is treated with 2 g (5.44 mmol) of the preceding hydrochloride 22.3 and then 1.51 ml (10.9 mmol) of triethylamine. After stirring for 1 h, the mixture is evaporated to dryness and treated as in Example 1.1 to give 1.88 g (Yd: 81%) of compound of formula 22.4:

(22-4)

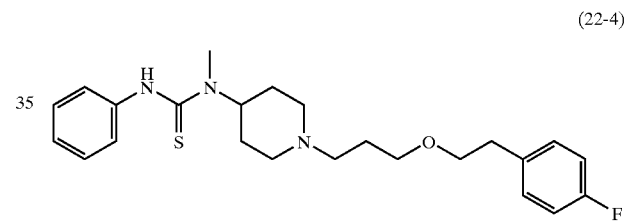

Empirical formula: $C_{24}H_{32}FN_3OS$

Molecular mass: 429.58

Off-white powder

NMR ($CDCl_3$) δ: 1.82–1.97 (m, 4H), 1.98–2.18 (m, 2H), 2.2–2.41 (m, 2H), 2.5–2.68 (m, 2H), 2.84 (t, 2H), 3.07 (s, 3H), 3.08–3.2 (m, 2H), 3.48 (t, 2H), 3.6 (t, 2H), 5.32 (m, 1H), 6.97 (t, 2H), 7.11 (s, 1H), 7.12–7.25 (m, 5H), 7.25–7.4 (m, 2H).

22.5) 1,2-Dimethyl-1-[1-[3-[2-(4-fluorophenyl)ethoxy]propyl]piperidin-4-yl]-3-phenylisothiourea hydrogen fumarate (22)

By carrying out the S-methylation of 1.76 g (4.1 mmol) of the preceding thiourea (22.4) with 281 μl (4.51 mmol) of methyl iodide according to the process of Example 1.2, 692 mg (Yd: 30%) of compound of formula 22 are prepared:

(22)

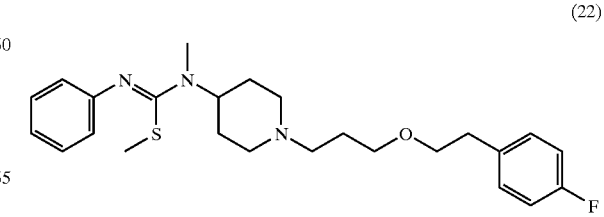

-continued

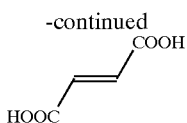

Empirical formula: $C_{29}H_{38}FN_3O_5S$
Molecular mass: 559.68
White powder
Melting point: 110–111° C.
NMR ($d_6$-DMSO) δ: 1.64–1.72 (m, 4H), 1.77–1.91 (m, 2H), 2 (s, 3H), 2.16 (t, 2H), 2.43 (t, 2H), 2.78 (t, 2H), 2.89 (s, 3H), 2.98–3.08 (m, 2H), 3.4 (t, 2H), 3.54 (t, 2H), 4.1–4.25 (m, 1H), 6.58 (s, 2H), 6.76 (d, 2H), 6.9 (m, 1H), 7.09 (m, 2H), 7.15–7.3 (m, 4H), 13 (m, 2H).

BIOLOGICAL EXPERIMENTS

The compounds of formula I, which are subject matters of the present invention, and their therapeutically acceptable salts have advantageous pharmacological properties.

These derivatives are active in the cardiomyocyte by inhibition of diastolic contraction induced by veratrine in the rat isolated left atrium. These compounds also reduce diastolic contraction during induced ischemia with respect to the guinea pig perfused isolated heart without affecting the base hemodynamic properties, which makes them highly selected products for ischemia.

These compounds are also active in vivo during ischemia-reperfusion in the anesthetized rabbit: they inhibit electrical disturbances of the ECG brought about by ischemia-reperfusion without a major hemodynamic effect; they are not cardiac depressants.

The molecules of the present invention are of use preventively or curatively in the treatment of coronaropathies, of all forms of angina and of all forms of cardiac and cerebral ischemia and in the treatment of atherosclerosis, cardiac insufficiency, epilepsy, pain and migraine.

1) Pharmacological study:

The experiments to which the chemical molecules which are a subject matter of the present invention have been subjected have made it possible to demonstrate a promising activity with regard to the cardiovascular system, both by "in vitro" and "in vivo" tests.

a) "in vitro" action:

The inhibition of the contraction with veratrine of the rat isolated left atrium was carried out according to the technique of Le Grand et al. (*Naunyn-Schmiedebergs Arch. Pharmacol.*, (1993) 348, p. 184–190). The results are shown in Table I below, where the percentages of the inhibition are given at a concentration of $10^{-7}$M.

TABLE I

| Compound | Ex. 1 | Ex. 3 | Ex. 13 | Ex. 21 | R 56865* | PF Control** |
|---|---|---|---|---|---|---|
| % contraction inhibition at $10^{-7}$M | 28% | 32% | 34% | 31% | 33% | 25% |

*N-(1-(4-(4-Fluorophenoxy)butyl)piperidin-4-yl)-N-methyl-2-benzothiazolamine, cited in Patent EP 0 184 257.
**N-[1-[4-(3,4-Difluorophenoxy)butyl]piperidin-4-yl]-N-methyl-4H-3,1-benzothiazin-2-amine, disclosed in Patent WO 97/05134.

The antiischemic activity was measured with regard to the test of the guinea pig perfused isolated heart according to the technique of Le Grand B. et al. (*Am. J. Physiol.*, 269, H533–H540, 1995). The guinea pig hearts are removed, perfused with a modified Krebs solution and the compound to be studied, in solution in water or in a 99/01 water/DMSO mixture (according to solubility), is added after 20 minutes. After minutes, global ischemia is brought about by halting coronary perfusion for 50 min, followed by reperfusion for 1 h. The inhibition of ischemic contraction in the presence of the compound studied is measured with respect to that of the vehicle group. The results are shown in Table II as nonlimiting examples at a concentration of $10^{-6}$M.

TABLE II

| Compound | Example 1 | Example 21 | PF Control** |
|---|---|---|---|
| % inhibition of the contraction at $10^{-6}$M | 69% | 53% | 48 |

**see Table I.

b) "in vivo" activity:

The compounds of the present invention are also active orally in the test of ischemia-reperfusion in the anesthetized rabbit according to the method of Verscheure et al., (*J. Cardiovasc. Pharmacol.*, 1995, 25, 126–133). The results for compound 1 are given as nonlimiting example in the following Table III:

TABLE III

| No. of the Product or Control | Dose mg/kg p.o. | % inhibition with regard to ST-segment elevation | Number of animals exhibiting reperfusion arrhythmias | % heart rate variation | % arterial pressure variation |
|---|---|---|---|---|---|
| 1 | 0.63 | 58% | 1/5 | 5 | −3 |
| PF Control** | 0.63 | 33% | 1/5 | 9 | 9 |
| R 56865* | 2.5 | 0% | 2/5 | 0 | 27 |

* and **: see Table I

2) Therapeutic applications:

The compounds of the present invention and their therapeutically acceptable salts are of use as medicaments.

These compounds are more particularly suitable in cardiology in the prophylactic treatment of cardiovascular diseases, such as:
 ischemia of the myocardium and coronaropathies and more particularly in crises:
  of chronic stable angina,
  of unstable and Prinzmetal's angina,
 silent ischemia, and in the prevention of reocclusions, restenoses and reinfarction;
 cerebral ischemia and more specifically in:
  strokes,
  transitory ischemic attack,
  neurodegenerative diseases,
 atherosclerosis,
 cardiac insufficiency,
 hypertension.

These compounds can also be used in the treatment of epilepsy, migraine and pain.

These compounds can be administered orally, parenterally or rectally. Each dose is composed of an inert adjuvant which promotes the preparation and absorption of the medicament; it being possible for the active principle also to be combined with another active principle.

These medicaments can be provided in the solid form (tablets or gelatin capsules) or liquid form to be prepared at the time of use (suspensions, emulsions, syrups, solutions or others) or in the form of suppositories. The active principle is administered at the mean dose of between 0.1 and 10 mg/kg of the weight of the body.

Two preparations are given as nonlimiting examples. The ingredients and other therapeutically acceptable ingredients can be introduced in other proportions without modifying the scope of the invention.

EXAMPLE 23

Injectable Solution
(to be prepared at the time of use)

| 1) A sterile bottle for injectable preparation made of inactinic glass having: | |
| --- | --- |
| 1,2-Dimethyl-1-[1-[4-(3,4-difluorophenoxy)butyl]piperidin-4-yl]-3-phenylisothiourea hydrogen fumarate | 10 mg |
| 2) A solvent vial made of sterile glass having | |
| Propylene glycol | 80 mg |
| Anhydrous dextrose | 40 mg |
| Sterile distilled water, q.s. for | 2 ml |

EXAMPLE 24

Tablets

| 1,2-Dimethyl-1-[1-[4-(3,4-difluorophenoxy)butyl]piperidin-4-yl]-3-phenylisothiourea hydrogen fumarate | 30 mg |
| --- | --- |
| Lactose hydrate | 90 mg |
| Microcrystalline cellulose | 20 mg |
| Magnesium stearate | 5 mg |
| Maize starch | 20 mg |
| Talc | 3 mg |
| Polyvinylpyrrolidone | 7 mg |
| Total weight | 175 mg |

What is claimed is:

1. A substituted 1,2-dialkyl-1-[1-(aryl(alkyl)oxyalkyl)-piperidin-4-yl]-3-arylisothiourea of formula I:

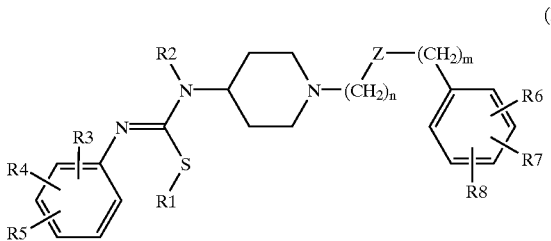

(I)

in which:
$R_1$ and $R_2$, which are identical or different, represent a saturated or unsaturated, branched or unbranched, alkyl radical having 1 to 7 carbon atoms,
$R_3$ to $R_8$, which are identical or different, represent:
a hydrogen,
a branched or unbranched alkyl having 1 to 5 carbon atoms,
a branched or unbranched alkyloxy having 1 to 5 carbon atoms,
a halo group,
a nitro group,
a hydroxyl group,
an acyl or acyloxy group comprising 1 to 5 carbon atoms,
a dialkylamino group having 1 to 5 carbon atoms,
a trifluoromethyl or trifluoromethoxy group,
Z represents an oxygen or sulfur atom or a methylene,
m represents an integer from 0 to 4 inclusive,
n represents an integer from 2 to 7 inclusive;
with the proviso that at least one of $R_3$ to $R_5$ and one of $R_6$ to $R_8$ is hydrogen, its pure enantiomers, mixtures, and therapeutically acceptable organic or inorganic salts.

2. A compound of claim 1 which is selected from the following compounds:

1,2-Dimethyl-3-phenyl-1-[1-[4-(3,4-difluorophenoxy)butyl]piperidin-4-yl]isothiourea hydrogen fumarate;
2-Ethyl-1-[1-[4-(3,4-difluorophenoxy)butyl]piperidin-4-yl]-1-methyl-3-phenylisothiourea hydrogen fumarate;
1-Ethyl-1-[1-[4-(3,4-difluorophenoxy)butyl]piperidin-4-yl]-2-methyl-3-phenylisothiourea hydrogen fumarate;
1-Isobutyl-1-[1-[4-(3,4-difluorophenoxy)butyl]piperidin-4-yl]-2-methyl-3-phenylisothiourea hydrogen fumarate;
1,2-Dimethyl-1-[1-[5-(3,4-difluorophenoxy)pentyl]piperidin-4-yl]-3-phenylisothiourea hydrogen fumarate;
1,2-Dimethyl-1-[1-[3-(3,4-difluorophenoxy)propyl]piperidin-4-yl]-3-phenylisothiourea hydrogen fumarate;
1,2-Dimethyl-1-[1-[4-(4-fluorophenoxy)butyl]piperidin-4-yl]-3-phenylisothiourea hydrogen fumarate;
1,2-Dimethyl-1-[1-[2-(4-fluorophenoxy)ethyl]piperidin-4-yl]-3-phenylisothiourea hydrogen fumarate;
1,2-Dimethyl-1-[1-[4-(4-methoxyphenoxy)butyl]piperidin-4-yl]-3-phenylisothiourea hydrogen fumarate;
1,2-Dimethyl-1-[1-[4-(3,4-dimethylphenoxy)butyl]piperidin-4-yl]-3-phenylisothiourea hydrogen fumarate;
1,2-Dimethyl-1-[1-[4-(2-methoxy-4-chlorophenoxy)butyl]piperidin-4-yl]-3-phenylisothiourea hydrogen fumarate;
1,2-Dimethyl-1-[1-[4-(3,4-difluorophenoxy)butyl]piperidin-4-yl]-3-(2-fluorophenyl)isothiourea hydrogen fumarate;
1,2-Dimethyl-1-[1-[4-(3,4-difluorophenoxy)butyl]piperidin-4-yl]-3-(4-fluorophenyl)isothiourea hydrogen fumarate;
1,2-Dimethyl-1-[1-[4-(3,4-difluorophenoxy)butyl]piperidin-4-yl]-3-(4-chlorophenyl)isothiourea hydrogen fumarate;
1,2-Dimethyl-1-[1-[4-(3,4-difluorophenoxy)butyl]piperidin-4-yl]-3-(4-methylphenyl)isothiourea hydrogen fumarate;
1,2-Dimethyl-1-[1-[4-(3,4-difluorophenoxy)butyl]piperidin-4-yl]-3-(4-methoxyphenyl)isothiourea hydrogen fumarate;
1,2-Dimethyl-1-[1-[4-(3,4-difluorophenoxy)butyl]piperidin-4-yl]-3-(2,6-dimethylphenyl)isothiourea hydrogen fumarate;
1,2-Dimethyl-1-[1-[4-(3,4-difluorophenoxy)butyl]piperidin-4-yl]-3-[2,6-diisopropylphenyl)isothiourea hydrogen fumarate;
1,2-Dimethyl-1-[1-[4-(3,4-difluorophenoxy)butyl]piperidin-4-yl]-3-(3-fluorophenyl)isothiourea hydrogen fumarate;
1,2-Dimethyl-1-[1-[4-(3,4-difluorophenoxy)butyl]piperidin-4-yl]-3-(4-nitrophenyl)isothiourea hydrogen fumarate;

1,2-Dimethyl-1-[1-[4-(3,4-difluorophenoxy)butyl]piperidin-4-yl]-3-(2,6-difluorophenyl)isothiourea hydrogen fumarate;

1,2-Dimethyl-1-[1-[3-[2-(4-fluorophenyl)ethoxy]propyl]piperidin-4-yl]-3-phenylisothiourea hydrogen fumarate.

3. Process for the preparation of a chemical compound of claim 1, wherein an isothiocyanate of formula (III):

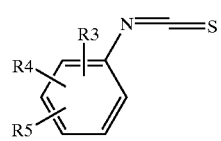
(III)

is reacted with a diamine of formula (II):

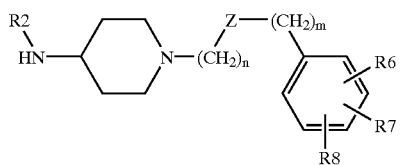
(II)

in a protic solvent, such as ethanol, or an aprotic solvent, such as THF or dioxane, by heating or not heating at reflux, to give the intermediate thiourea of formula (IV):

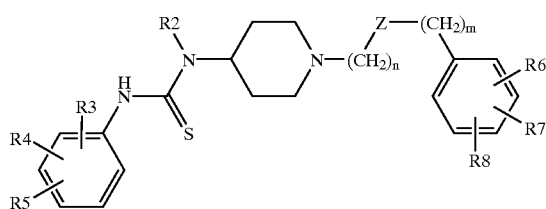
(IV)

which is subsequently S-alkylated with a halide $R_1Br$ or $R_1I$ or an alkyl sulfate $(R_1)_2S_4$ in a protic solvent, such as alcohol, or an aprotic solvent, such as THF, DMF or ethyl acetate, with or without the presence of lime at a temperature between 20 and 60° C., to give the compound I of the present invention, it being understood that the formulae II, III and IV, the $R_1$ to $R_8$ and Z radicals and the numbers m and n have the same values as in claim 1.

4. A pharmaceutical composition which contains as active principle a compound of claim 1, combined with an inert pharmaceutical support, or other pharmaceutically-acceptable vehicles, which may be combined with another medicinal product.

5. A method of treating a living body afflicted with a condition requiring the prophylactic treatment of myocardial ischemia selected from chronic stable angina, unstable angina and Prinzmetal's angina attacks, silent ischemia, reinfarction, reocclusion and restenosis, comprising the step of administering an effective amount of a compound of claim 1 to a patient in need thereof.

6. A method-of-treating atherosclerosis in a living body comprising the step of administering an effective amount of a compound of claim 1 to a patient in need thereof.

7. A method-of-treating a living body afflicted with a condition selected from cardiac insufficiency and hypertension comprising the step of administering an effective amount of a compound of claim 1 to a patient in need thereof.

* * * * *